US008535884B2

(12) United States Patent
Eriksson et al.

(10) Patent No.: US 8,535,884 B2
(45) Date of Patent: Sep. 17, 2013

(54) *LMNA* GENE AND ITS INVOLVEMENT IN HUTCHINSON-GILFORD PROGERIA SYNDROME (HGPS) AND ARTERIOSCLEROSIS

(75) Inventors: B. Maria H. Eriksson, Solna (SE); Francis S. Collins, Rockville, MD (US); Leslie B. Gordon, Foxboro, MA (US); W. Ted Brown, Staten Island, NY (US)

(73) Assignees: The United States of America as represented by the Secretary of the Department of Health and Human Services, Washington, DC (US); Research Foundation for Mental Hygiene, Inc., Menands, NY (US); The Progeria Research Foundation, Inc., Peabody, MA (US)

( * ) Notice: Subject to any disclaimer, the term of this patent is extended or adjusted under 35 U.S.C. 154(b) by 37 days.

(21) Appl. No.: 13/229,441

(22) Filed: Sep. 9, 2011

(65) Prior Publication Data

US 2012/0045762 A1 Feb. 23, 2012

Related U.S. Application Data

(60) Continuation of application No. 11/870,234, filed on Oct. 10, 2007, now Pat. No. 8,034,557, which is a division of application No. 10/943,400, filed on Sep. 17, 2004, now Pat. No. 7,297,492, which is a continuation of application No. PCT/US03/33058, filed on Oct. 17, 2003.

(60) Provisional application No. 60/463,084, filed on Apr. 14, 2003, provisional application No. 60/419,541, filed on Oct. 18, 2002.

(51) Int. Cl.
*C12Q 1/68* (2006.01)
*C07H 21/04* (2006.01)
*C07H 21/02* (2006.01)

(52) U.S. Cl.
USPC .......................................... 435/6.1; 536/24.3

(58) Field of Classification Search
None
See application file for complete search history.

(56) References Cited

U.S. PATENT DOCUMENTS

| | | | |
|---|---|---|---|
| 6,060,038 A | 5/2000 | Burns et al. | |
| 6,342,487 B1 | 1/2002 | Riou et al. | |
| 6,737,410 B1 | 5/2004 | Doherty et al. | |
| 2002/0044941 A1 | 4/2002 | Rosen et al. | |
| 2002/0098495 A1 | 7/2002 | Burmer et al. | |
| 2003/0125326 A1 | 7/2003 | Rybak | |
| 2004/0110769 A1 | 6/2004 | End | |

FOREIGN PATENT DOCUMENTS

| | | |
|---|---|---|
| WO | WO 97/30053 | 8/1997 |
| WO | WO 01/64218 | 9/2001 |
| WO | WO 02/04662 | 1/2002 |

OTHER PUBLICATIONS

"Lamin A/C (LMNA)" *Leiden Muscular Dystrophy pages* © (Sep. 8, 2008), http://www.dmd.nl/lmna_home.html.
Adjei et al., "Comparison of Potential Markers of Farnesyl Transferase Inhibition," *Clinical Cancer Res.*, 6: 2318-2325, 2000.
AH001498 Human nuclear lamin A and nuclear lamin C gene, Feb. 11, 2000. *NCBI* printed Oct. 17, 2002.
Bonne et al., "Clinical and Molecular Genetic Spectrum of Autosomal Dominant Emery-Dreifuss Muscular Dystrophy due to Mutations of the Lamin A/C Gene," *Annals of Neurology*, 48(2): 170-180, 2000.
Bonne et al., "Mutations in the gene encoding lamin A/C cause autosomal dominant Emery-Dreifuss muscular dystrophy," *Nature Genetics*, 21(3): 285-288, 1999.
Burke and Stewart, "Life at the Edge: The Nuclear Envelope and Human Disease," *Molecular Cell Biology—Nature Reviews* 3: 575-585, 2002.
Cao and Hegele, "*LMNA* is mutated in Hutchinson-Gilford progeria (MIM 176670) but not in Wiedemann-Rautenstrauch progeroid syndrome (MIM 264090)," *J. Hum. Genet.* 48: 271-274, 2003.
Cao et al., "LMNA in mutated in Hutchinson-Gilford progeria (MIM 176670) but not in Wiedemann-Rautenstrauch progeroid syndrome (MIM 264090)," *J. Hum. Genet.*, 48: 271-271, 2003.
Cohen et al., "Inhibitors of Prenylation of Ras and Other G-proteins and Their Application as Therapeutics," *Biochem. Pharm.*, 60: 1061-1068, 2000.
Cox and Der, "Farnesyltransferase inhibitors: promises and realities," *Curr. Opin. Pharm.* 2: 388-393, 2002.
Database EMBL (online), "*Homo sapiens* lamin A/C, transcript variant 1, mRNA (cDNA clone MGC:23638 Image:4863480), complete cds," Accession No. BC014507, Sep. 24, 2001.
Database UniProt (online), "Lamin A/C (70 kDa Lamin)," Accession No. P02545, Jul. 21, 1986.

(Continued)

*Primary Examiner* — Nancy T Vogel
(74) *Attorney, Agent, or Firm* — Klarquist Sparkman LLP

(57) ABSTRACT

Disclosed herein are point mutations in the LMNA gene that cause HGPS. These mutations activate a cryptic splice site within the LMNA gene, which leads to deletion of part of exon 11 and generation of a mutant Lamin A protein product that is 50 amino acids shorter than the normal protein. In addition to the novel Lamin A variant protein and nucleic acids encoding this variant, methods of using these molecules in detecting biological conditions associated with a LMNA mutation in a subject (e.g., HGPS, arteriosclerosis, and other age-related diseases), are also described. Oligonucleotides and other compounds for use in examples of the described methods are also provided, as are protein-specific binding agents, such as antibodies, that bind specifically to at least one epitope of a Lamin A variant protein preferentially compared to wildtype Lamin A, and methods of using such antibodies in diagnosis, treatment, and screening.

4 Claims, 6 Drawing Sheets

(56) References Cited

OTHER PUBLICATIONS

De Sandre-Giovannoli et al., "Homozygous Defects in LMNA, Encoding Lamin A/C Nuclear-Envelope Proteins, Cause Autosomal Recessive Axonal Neuropathy in Human (Charcot-Marie-Tooth Disorder Type 2) and Mouse," *Am. J. Hum. Genet.*, 70(3): 726-736, 2002.
De Sandre-Giovannoli, et al., "Lamin A Truncation in Hutchinson-Gilford Progeria," *Science*, 300(4): 2055, 2003.
Delahunt et al., "Progeria kidney has abnormal mesangial collagen distribution," *Pediatr. Nephrol.*, 15: 279-285, 2000.
Eriksson et al., "Recurrent de novo point mutations in lamin A cause Hutchinson-Gilford Progeria Syndrome," *Nature*, 423: 293-298, 2003.
Faivre et al., "Can Hutchinson-Gilford Progeria Syndrome be a Neonatal Condition?" *Letter to the Editor—Am. J. Med. Genet.* 87:450-452, 1999.
Fisher et al., "cDNA sequencing of nuclear lamins A and C reveals primary and secondary structural homology to intermediate filament proteins," *Proc. Natl. Acad. Sci. USA*, 83: 6450-6454, 1986.
Fong et al., "Heterozygosity for *LMNA* deficiency eliminates the progeria-like phenotypes in *Zmpste24*-deficient mice," *Proc. Natl. Sci. Acad. USA*, 101(52): 18111-18116, 2004.
Garcia et al., "Peptidomimetic Inhibitors of Ras Farnesylation and Function in Whole Cells," *J. Biol. Chem.*, 268(25): 18415-18418, 1993.
Genschel et al., "Mutations in the LMNA Gene Encoding Lamin A/C," *Human Mutation*, 16(6): 451-459, 2000.
Goldman et al., "Accumulation of mutant lamin A causes progressive changes in nuclear architecture in Hutchinson-Gilford progeria syndrome," *Proc. Natl. Acad. Sci. USA*, 101(24): 8963-8968, 2004.
Hae et al., "Cardiovascular Findings of Hutchinson-Gilford Syndrome—A Doppler and two-dimensional Echocardiographic study--," *Yonset Med. J.* 34(4): 352-355, 1993.
Hegele et al., "Common Genomic Variation in LMNA Modulates Indexes of Obesity in Inuit," *J. of Clinical Endocrinology and Metabolism*, 86(6): 2747-2751, 2001.
Hegele, "Premature Atherosclerosis Associated with Monogenic Insulin Resistance," *Circulation—Clinical Invest. and Rep.*, 103(18): 2225-2229, 2001.
Hegele, "Premature Atherosclerosis Associated with Monogenic Insulin Resistance," *Circulation*, 103(18): 2225-2229, 2001.
Henig, "Racing with Sam," *The New York Times Magazine*, 46-51, 2005.
Hoeffel et al., "Mandibulo-acral dysplasia," *Skeletal Radiol.*, 29: 668-671, 2000.
Hoover et al., "Overcoming STI571 resistance with the farnesyl transferase inhibitor SCH66336," *Blood*, 100(3): 1068-1071, 2002.
Hutchinson, "Lamins: Building Blocks or Regulators of Gene Expression?" *Molecular Cell Biology*, 3(11): 848-858, 2002.
Ikeda and Shimada, Pleiotropic Effects of Statins on the Vascular Tissue, *Current Drug Targets—Cardiovascular & Haematological Disorders*, 1(1): 51-58, 2001.
Jansen and Romiti, "Progeria Infantum (Hutchinson-Gilford Syndrome) Associated with Scleroderma-Like Lesions and Acro-Osteolysis: A Case Report and Brief Review of the Literature," *Pediatric Dermatology*, 17(4): 282-285, 2000.
L12401 Human nuclear lamin A and nuclear lamin gene, exons 3-12 and complete alternative mRNAs, Feb. 11, 2000. *NCBI* printed Oct. 17, 2002.
Lutz et al., "Nucleoplasmic localization of prelamin A: Implications for prenylation-dependent lamin A assembly into the nuclear lamina," *Proc. Natl. Acad. Sci. USA*, 89: 3000-3004, 1992.
Ly et al., "Mitotic Misregulation and Human Aging," *Science*, 287: 2486-2492, 2000.
Machiels et al., "An Alternative Splicing Product of the Lamin A/C Gene Lacks Exon 10," *J. of Biological Chemistry*, 271(16): 9249-9253, 1996.
Maske et al., "A carboxyl-terminal interaction of lamin B1 is dependent on the CAAX endoprotease Rce1 and carboxymethylation," *J. Cell Biol.*, 162(7): 1223-1232, 2003.
McKeon et al., "Homologies in both primary and secondary structure between nuclear envelope and intermediate filament proteins," *Nature*, 319: 463-468, 1986.
Mégnin-Chanet et al., "The farnesyl transferase inhibitor RPR-130401 does not alter radiation susceptibility in human tumor cells with a K-Ras mutation in spite of large changes in ploidy and lamin B distribution," *BMC Pharm.*, 2: 2, 2002.
Nalbone et al., "Statins: Maid-of-all-work in Cardiovascular Diseases!" *Archives Des Maladies Du Coeur Et Des Vaisseaux*, 96(3): 207-213, 2003.
Novelli et al., "Mandibuloacral Dysplasia is Caused by a Mutation in *LMNA*-Encoding Lamin A/C," *Am. J. Hum. Genet.*, 71: 426-431, 2002.
P02545 Lamin A/C (70 kDa lamin), Jun. 15, 2002. *NCBI* printed Oct. 17, 2002.
Pesce and Rothe, "The Premature Aging Syndromes," *Clinics in Dermatology*, 14: 161-170, 1996.
Peters et al., "Activity of the farnesyl protein transferase inhibitor SCH66336 against BCR/ABL-induced murine leukemia and primary cells from patients with chronic myeloid leukemia," *Blood*, 97(5): 1404-1412, 2001.
Pollex et al., "Hutchinson-Gilford progeria syndrome," *Clin.. Genet.*, 66: 375-381, 2004.
Rodríguez and Pérez-Alonso, "Diagnosis of Progeria Syndrome is the Only One Possible," *Letter to the Editor—Am. J. Med. Genet.*, 87: 453-454, 1999.
Rodríguez et al., "Lethal Neonatal Hutchinson-Gilford Progeria Syndrome," *Am. J. Med. Genet.*, 82: 242-248, 1999.
Rosenblum et al., "On signal sequence polymorphisms and diseases of distribution," *Proc. Natl. Acad. Sci. USA*, 93: 4471-4473, 1996.
Sarkar and Shinton, "Hutchinson-Gilford progeria syndrome," *Postgrad Med J.*, 77: 312-317, 2001.
Stoneking et al., "Population Variation of Human mtDNA Control Region Sequences Detected by Enzymatic Amplification and Sequence-specific Oligonucleotide Probes," *Am. J. Hum. Genet.*, 48: 370-382, 1991.
Uitto "Searching for clues to premature aging," *Trends in Endocrinology & Metabolism* 13(4): 140-141, 2004.

Case #1
46,XY UPD (1)(p11.2;qter)

Case #2
46,XX UPD (1)(q22;qter)

| | | Case #1 | | Case #2 | |
|---|---|---|---|---|---|
| 1p13.1 | D1S252 | 96 | 102 | 92 | 106 |
| 1p11.2 | D1S2696 | 173 | 173 | ← 1p11.2 | 167 169 |
| 1q21.1 | D1S2344 | 255 | 255 | 253 | 255 |
| 1q21.2 | D1S2222 | 148 | 148 | 148 | 148 |
| 1q21.3 | D1S498 | 206 | 206 | 198 | 202 |
| 1q21.3 | D1S2347 | 272 | 272 | 272 | 284 |
| 1q21.3 | D1S2346 | 111 | 111 | 99 | 107 |
| 1q22 | D1S1153 | 304 | 304 | 305 305 ← 1q22 | |
| 1q23.1 | D1S1653 | 108 | 108 | 104 | 104 |
| 1q23.2 | D1S2635 | 149 | 149 | 146 | 146 |
| 1q24.2 | D1S196 | 332 | 332 | 330 | 330 |
| 1q25.2 | D1S2791 | 172 | 172 | 172 | 172 |
| 1q25.3 | D1S2127 | 124 | 124 | 128 | 128 |
| 1q31.1 | D1S191 | 159 | 159 | 163 | 163 |
| 1q31.3 | D1S413 | 260 | 260 | 260 | 260 |
| 1q32.2 | D1S2685 | 109 | 109 | 115 | 115 |
| 1q41 | D1S2141 | 259 | 259 | 263 | 263 |
| 1q42.12 | D1S2763 | 169 | 169 | 169 | 169 |
| 1q42.2 | D1S2800 | 219 | 219 | 215 | 215 |
| 1q43 | D1S2850 | 153 | 153 | 155 | 155 |
| 1q44 | D1S2836 | 246 | 246 | 249 | 249 |

46 XY, inv ins (1;1)(q32;q44q23)

Schematic representation of the *LMNA* gene encoding lamin A and lamin C proteins, showing position of disease-causing mutations Expert Reviews in Molecular Medicine © 2002 Cambridge University Press

Previously Known Mutations in Lamin A/C

LMNA GENE AND ITS INVOLVEMENT IN HUTCHINSON-GILFORD PROGERIA SYNDROME (HGPS) AND ARTERIOSCLEROSIS

CROSS REFERENCE TO RELATED APPLICATIONS

This is a continuation of co-pending U.S. application Ser. No. 11/870,234, filed Oct. 10, 2007, which issued as U.S. Pat. No. 8,034,557 on Oct. 11, 2011, which is a divisional of U.S. application Ser. No. 10/943,400, filed Sep. 17, 2004, which issued as U.S. Pat. No. 7,297,492 on Nov. 20, 2007, which is a continuation of PCT/US2003/0033058, filed Oct. 17, 2003, which in turn claims the benefit of U.S. Provisional Application 60/463,084, filed Apr. 14, 2003, and U.S. Provisional Application 60/419,541, filed Oct. 18, 2002. All of these applications are incorporated herein in their entirety.

FIELD OF THE DISCLOSURE

This disclosure relates to genetic bases of aging, and more particularly to the gene LMNA, which encodes Lamin A/C, and its involvement in aging phenomena including the disease referred to as Hutchinson-Gilford Progeria Syndrome (HGPS).

BACKGROUND OF THE DISCLOSURE

The prospect of reversing senescence and restoring the proliferative potential of cells has implications in many fields of endeavor. Many of the diseases of old age are associated with the loss of this potential. Moreover, the tragic disease, Progeria, which is often described in the literature as a premature aging syndrome based on appearance, is associated with the loss of proliferative potential of cells. Werner Syndrome and Hutchinson-Gilford Progeria Syndrome (HGPS) are two progeroid diseases. A major clinical difference between the two is that the onset of Hutchinson-Gilford Progeria Syndrome (sometimes called progeria of childhood) occurs within the first decade of life, whereas the first evidence of Werner Syndrome (sometimes called progeria of adulthood) appears only after puberty, with the full symptoms becoming manifest in individuals 20 to 30 years old.

More particularly, Hutchinson-Gilford Progeria Syndrome (HGPS) (also referred to as Hutchinson-Gilford Syndrome or Progeria) is a very rare progressive disorder of childhood characterized by features of premature aging (progeria), failure to thrive usually beginning in the first year of life resulting in short stature and low weight, deterioration of the layer of fat beneath the skin (subcutaneous adipose tissue), and characteristic craniofacial abnormalities, including frontal bossing, underdeveloped jaw (micrognathia), unusually prominent eyes and/or a small, "beak-like" nose. In addition, during the first year or two of life, scalp hair, eyebrows and eyelashes may become sparse, and veins of the scalp may become unusually prominent. Additional symptoms and physical findings may include joint stiffness, repeated nonhealing fractures, a progressive aged appearance of the skin, delays in tooth eruption (dentition) and/or malformation and crowding of the teeth. Individuals with the disorder typically have normal intelligence. In most cases, affected individuals experience premature, widespread thickening and loss of elasticity of artery walls (arteriosclerosis), often resulting in life-threatening complications such as heart attacks and strokes which are the usual causes of death.

HGPS is thought to be a genetic disorder, yet the mode of inheritance, molecular basis, and pathogenic mechanism all remain elusive. It has in the past been thought to be due to a sporadic autosomal dominant genetic mutation.

The identification of mutations associated with HGPS would be an incredible breakthrough in detection, diagnosis, and prognosis of this disease, and would open avenues for treatment and possibly prevention of HGPS and related or similar conditions, including more generally arteriosclerosis and aging.

SUMMARY OF THE DISCLOSURE

Surprisingly, point mutations have been identified in the LMNA gene that cause HGPS. The inheritance is new mutation autosomal dominant, and identified mutations occur in codon 608; the most common is due to a C to T base substitution in a CpG dinucleotide. It is currently believed that the mechanism of the mutations is activation of a cryptic splice site within the LMNA gene, which leads to deletion of part of exon 11 and generation of a Lamin A protein product that is 50 amino acids shorter than the normal protein. All of the identified mutations are predicted to affect Lamin A but not Lamin C. In addition, two cases of segmental UPD from fibroblast DNA do not show the mutation, which may be indicative of a (in vivo or in vitro) somatic rescue event.

Thus, this disclosure provides a novel Lamin A variant protein, and nucleic acids encoding this variant. Also disclosed are methods of using these molecules in detecting biological conditions associated with a LMNA mutation in a subject (e.g., HGPS, arteriosclerosis, and other age-related diseases), methods of treating such conditions, methods of selecting treatments (e.g., agents that promote mitotic crossing over and thereby somatic rescue events), methods of screening for compounds that influence Lamin A activity, and methods of influencing the expression of LMNA or LMNA variants. Oligonucleotides and other compounds for use in examples of such methods are also provided.

Also disclosed herein are protein-specific binding agents, such as antibodies, that bind specifically to at least one epitope of a Lamin A variant protein preferentially compared to wildtype Lamin A, and methods of using such antibodies in diagnosis, treatment, and screening.

Kits are also provided for carrying out the methods described herein.

The foregoing and other features and advantages will become more apparent from the following detailed description of several embodiments, which proceeds with reference to the accompanying figures.

The identified deleted region contains approximately 80 genes, one of which is LMNA (encoding Lamin A/C), which is illustrated.

Figure 2A:
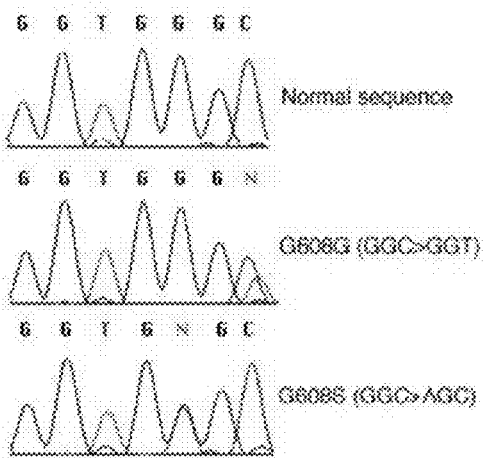

FIG. 2A is a series of sequencing results, illustrating heterozygote base substitutions in LMNA. The top sequence trace shows the normal sequence surrounding codon 608 of LMNA; the middle trace is the same region in one of the HGPS samples; the third panel shows the sequence trace from sample AG10801. Heterozygote nucleotides are indicated with an N.

Figure 2B:
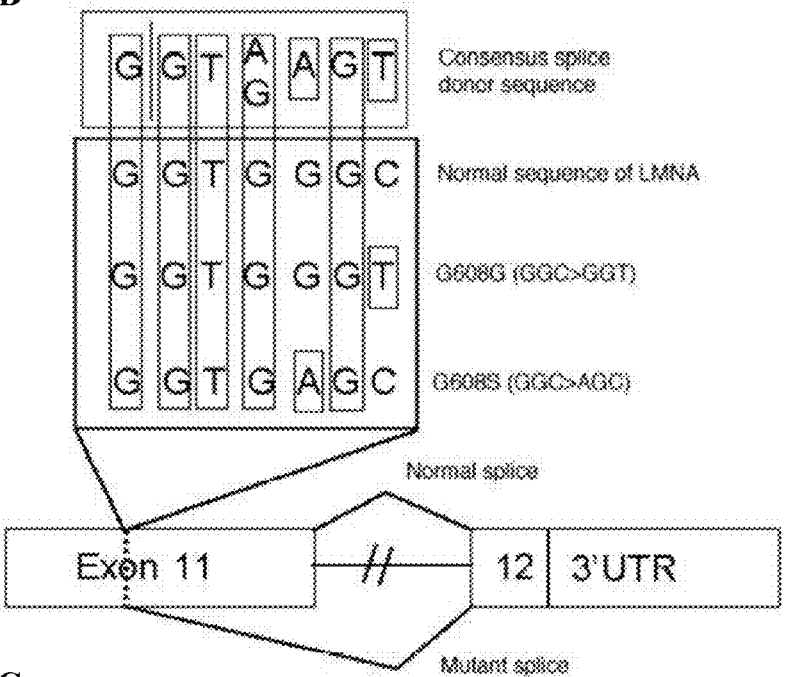

FIG. 2B illustrates the mechanism of activation of a cryptic splice donor site in exon 11, which occurs in the two mutations codon 608 identified herein. These mutations (designated as Mutation 1 and Mutation 2 in the figure) activate a cryptic splice site within exon 11, thereby altering the structure of the resultant protein while seemingly appearing "silent" on first examination. The consensus sequence for a splice donor is as listed at the top of the figure.

The normal sequence, which is also the sequence that was found in all the unaffected first degree relatives, shows two mismatches to the consensus splice sequence. Mutation 1, which is the more common of the two mutations identified to date, changes this sequence to just one mismatch. Mutation 2 does the same, by altering the other nucleotide.

Activation of the cryptic splice site within exon 11 results in part of exon 11 being deleted from the mRNA sequence. Exon 12 is still in frame, so the resulting Lamin A protein has an internal deletion of exactly 50 amino acids.

Figure 2C:
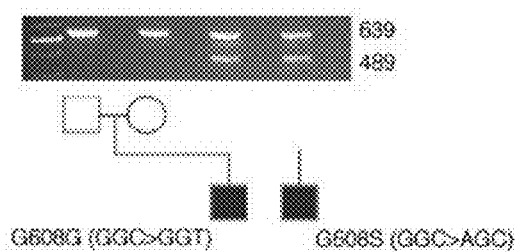

FIG. 2C is a picture of a DNA gel, showing the results of an RT-PCR experiment on representative samples. The normal product is seen at 639 bp, but a product of 489 bp is also seen in the two HGPS probands (AG03506 and AG10801), due to activation of the cryptic splice site. Alternate lanes contain RT-PCR product from controls using no reverse transcriptase.

Figure 3:
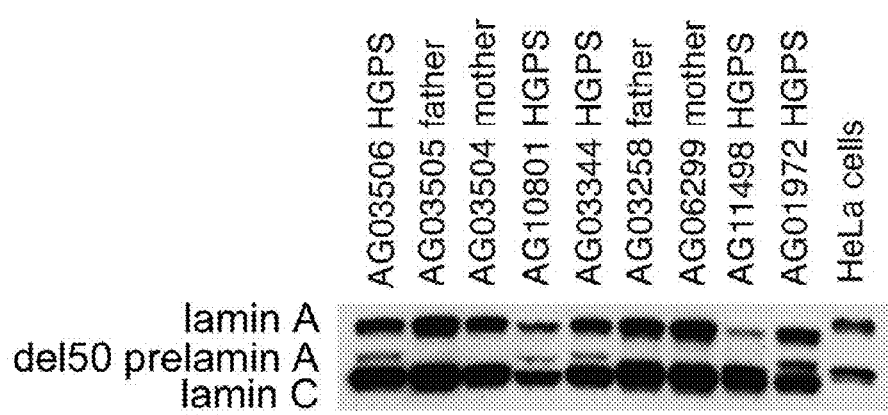

FIG. 3 is a Western blot using a monoclonal antibody against Lamin A/C. Protein samples originating from EBV-transformed lymphoblastoid cell lines are in the first five lanes. Protein samples originating from primary dermal fibroblasts are in the next four lanes. The samples marked "AG03505 father" and "AG03504 mother" are derived from the parents of the HGPS sample AG03506. A protein sample from HeLa cells was used as positive control; the slightly different migration of Lamin A and Lamin C in this lane is presumed to be due to a difference in post-translational modification.

Figure 4:
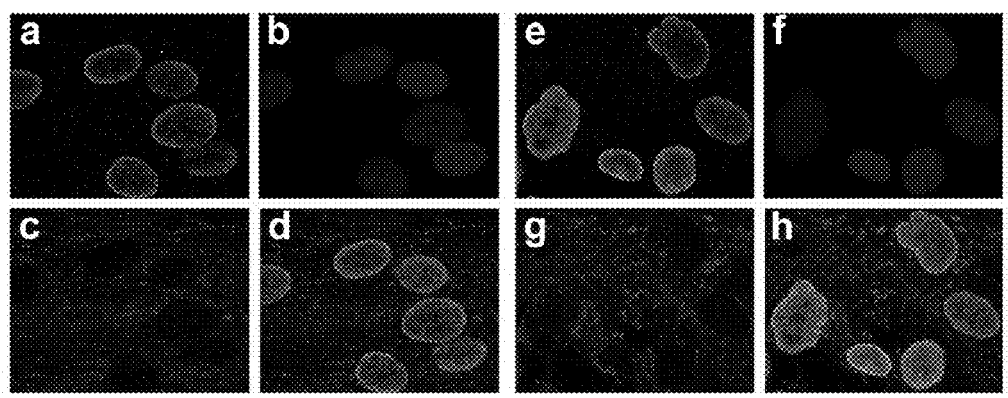

FIG. 4 is a series of micrographs, illustrating Immunofluorescence on primary dermal fibroblasts from an unaffected mother and child with classical HGPS, using antibody JOL2 against Lamin A/C. Identical results were obtained with antibody XB10. FIG. 4A-4D show results from an unaffected mother, AG06299. FIG. 4E-4H show results from a classical HGPS patient, AG11498. In FIGS. 4A and 4E, the antibody is against Lamin A/C. In FIGS. 4B and 4F, the cells are DAPI stained, showing location of the nuclei. In FIGS. 4C and 4B, the antibody stains mitochondria, showing distribution of the cytosol. FIG. 4D is a merged image of FIG. 4A-4C. FIG. 4H is a merged image of FIG. 4E-4G.

Figure 5A:
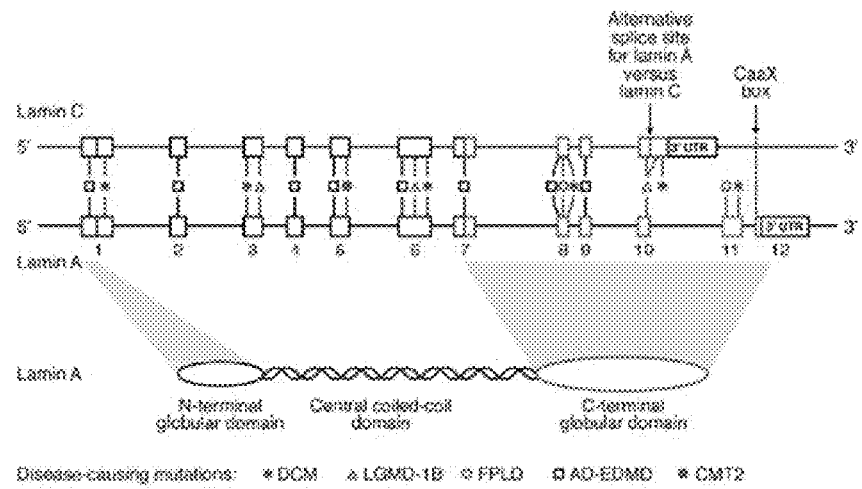
Figure 5B:
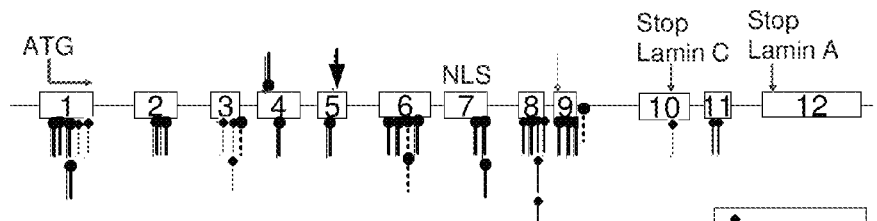

FIG. 5 provides two schematic representations of the LMNA gene encoding Lamin A and Lamin C proteins, showing position of disease-causing mutations (FIGS. 5A and 5B) and the schematic structure of the protein (FIG. 5A).

The LMNA gene has 12 exons, which are shown here as boxes. The predicted structural motifs of lamin A are shown as two globular domains, one at the N- and one at the C-terminus, with a central coiled-coil region linking the two (FIG. 5A).

The figure shows the exons affected by disease rather than the individual mutations. Mutations causing autosomal dominant Emery-Dreifuss muscular dystrophy (AD-EDMD) occur along the length of the LMNA gene. Mutations causing dilated cardiomyopathy (DCM) have been found in exons 1, 3, 6, 8, 10 and 11; mutations linked with familial Dunnigan-type partial lipodystrophy (FPLD) occur in exons 8 and 11; mutations linked with limb-girdle muscular dystrophy 1B (LGMD-1B) occur in exons 3, 6 and 10; and one mutation linked to Charcot-Marie-Tooth disorder type 2 (AR-CMT2) occurs in exon 5. There is also a mandibuloacral dysplasia recessive mutation in exon 9.

BRIEF DESCRIPTION OF THE SEQUENCES

The nucleic and amino acid sequences listed herein are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named SeqList-66648-11.txt, created on Sep. 6, 2011, ~47.5 KB, which is incorporated by reference herein. In the accompanying sequence listing:

SEQ ID NO: 1 shows the nucleic acid sequence and deduced amino acid sequence of normal (wildtype) LMNA. This sequence is derived from AH001498, but modified according to Fisher et al. (*PNAS USA*, 83: 6450-6454, 1986) at codon positions 555 and 556; the corrected cDNA sequences are also shown in GenBank Accession Nos. NM_170707 (Lamin A) and NM_005572 (Lamin C). The genomic DNA sequence and mRNA sequence (exon 3-12) of LMNA are shown in GI 292250 (same as accession number L12401). In addition, all of the LMNA exons (1, 2, and 3-12) as well as 5' and 3' UTRs are found in Accession No. AH001498.

SEQ ID NO: 2 shows the amino acid sequence of the normal Lamin A protein.

SEQ ID NO: 3 shows the nucleic acid sequence of normal exon 11 of LMNA.

SEQ ID NO: 4 shows the nucleic acid sequence of exon 11 of LMNA with Mutation 1 (also referred to as G608G (GGC>GGT)).

SEQ ID NO: 5 shows the nucleic acid sequence of exon 11 of LMNA with Mutation 2 (also referred to as G608S (GGC>AGC)).

SEQ ID NO: 6 shows the predicted cDNA (and deduced amino acid sequence encoded thereby) resulting from intron/exon processing of either Mutation 1 (G608G(GGC>GGT)) and Mutation 2 (G608S(GGC>AGC)), which lead to the same predicted mutant cDNA sequence. This sequence lacks 150 nucleotides of the wildtype LMNA cDNA that are spliced away due to the activation of a cryptic splice site within exon 11.

SEQ ID NO: 7 shows the amino acid sequence of mutant Lamin A protein encoded by the cDNA in either Mutation 1 or Mutation 2 samples. This protein is 50 amino acids shorter than the normal Lamin A, shown in SEQ ID NO: 2.

SEQ ID NOs: 8-57 show the nucleic acid sequence of primers used for analysis of microsatellite markers on chromosome 1q21.3-23.1 (as described in Table 1).

SEQ ID NOs: 58-63 show the nucleic acid sequence of primers used for mutation analysis of LMNA.

SEQ ID NOs: 64 and 65 show the nucleic acid sequence of primers used for RT-PCR analysis of exon 11.

SEQ ID NO: 66 is the CAAX box motif of the prelamin protein.

DETAILED DESCRIPTION

I. Abbreviations

ASO: allele-specific oligonucleotide
ASOH: allele-specific oligonucleotide hybridization
DASH: dynamic allele-specific hybridization
DEXA: dual energy X-ray absorptiometry
HGPS: Hutchinson-Gilford Progeria Syndrome
RT-PCR: reverse-transcription polymerase chain reaction

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). A comprehensive discussion of aspects of Hutchinson-Gilford Progeria syndrome and terms relevant to this syndrome can be found, for instance, in DeBusk (*J. Pediatrics*, 80:697-724, 1974).

In order to facilitate review of the various embodiments of the invention, the following non-limiting explanations of specific terms are provided:

Abnormal: Deviation from normal characteristics. Normal characteristics can be found in a control, a standard for a population, etc. For instance, where the abnormal condition is a disease condition, such as progeria, a few appropriate sources of normal characteristics might include an individual who is not suffering from the disease (e.g., progeria), a population standard of individuals believed not to be suffering from the disease, etc.

Likewise, abnormal may refer to a condition that is associated with a disease. The term "associated with" includes an increased risk of developing the disease as well as the disease itself. For instance, a certain abnormality (such as an abnormality in an LMNA nucleic acid or Lamin protein expression) can be described as being associated with the biological conditions of progeria and tendency to develop premature aging disease or condition.

An abnormal nucleic acid, such as an abnormal LMNA nucleic acid, is one that is different in some manner to a normal (wildtype) nucleic acid. Such abnormality includes but is not necessarily limited to: (1) a mutation in the nucleic acid (such as a point mutation (e.g., a single nucleotide polymorphism) or short deletion or duplication of a few to several nucleotides); (2) a mutation in the control sequence(s) associated with that nucleic acid such that replication or expression of the nucleic acid is altered (such as the functional inactivation of a promoter); (3) a decrease in the amount or copy number of the nucleic acid in a cell or other biological sample (such as a deletion of the nucleic acid, either through selective gene loss or by the loss of a larger section of a chromosome or under expression of the mRNA); (4) an increase in the amount or copy number of the nucleic acid in a cell or sample (such as a genomic amplification of part or all of the nucleic acid or the overexpression of an mRNA), each compared to a control or standard; and (5) an alteration in a sequence that controls the splicing mechanism, in such a way that either a normal splice signal is inactivated or an abnormal splice signal is created. It will be understood that these types of abnormalities can co-exist in the same nucleic acid or in the same cell or sample; for instance, a genomic-amplified nucleic acid sequence may also contain one or more point mutations. In addition, it is understood that an abnormality in a nucleic acid may be associated with, and in fact may cause, an abnormality in expression of the corresponding protein.

Abnormal protein expression, such as abnormal Lamin A protein expression, refers to expression of a protein that is in some manner different to expression of the protein in a normal (wildtype) situation. This includes but is not necessarily limited to: (1) a mutation in the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of an increased amount of the protein, compared to a control or standard amount; (5) expression of a decreased amount of the protein, compared to a control or standard amount; (6) alteration of the subcellular localization or targeting of the protein; (7) alteration of the temporally regulated expression of the protein (such that the protein is expressed when it normally would not be, or alternatively is not expressed when it normally would be); and (8) alteration of the localized (e.g., organ or tissue specific) expression of the protein (such that the protein is not expressed where it would normally be expressed or is expressed where it normally would not be expressed), each compared to a control or standard.

Controls or standards appropriate for comparison to a sample, for the determination of abnormality, include samples believed to be normal as well as laboratory values, even though possibly arbitrarily set, keeping in mind that such values may vary from laboratory to laboratory. Laboratory standards and values may be set based on a known or determined population value and may be supplied in the format of a graph or table that permits easy comparison of measured, experimentally determined values.

Antisense, Sense, and Antigene: Double-stranded DNA (dsDNA) has two strands, a 5'→3' strand, referred to as the plus strand, and a 3'→5' strand (the reverse complement), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Binding or stable binding (of an oligonucleotide): An oligonucleotide binds or stably binds to a target nucleic acid if a sufficient amount of the oligonucleotide forms base pairs or is hybridized to its target nucleic acid, to permit detection of that binding. Binding can be detected by either physical or functional properties of the target:oligonucleotide complex. Binding between a target and an oligonucleotide can be detected by any procedure known to one skilled in the art, including both functional and physical binding assays. Binding may be detected functionally by determining whether binding has an observable effect upon a biosynthetic process such as expression of a gene, DNA replication, transcription, translation and the like.

Physical methods of detecting the binding of complementary strands of DNA or RNA are well known in the art, and include such methods as DNAse I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with the bases in a second nucleic acid strand. Complementarity is conveniently described by percentage, e.g. the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

A thorough treatment of the qualitative and quantitative considerations involved in establishing binding conditions that allow one skilled in the art to design appropriate oligonucleotides for use under the desired conditions is provided by Beltz et al. *Methods Enzymol* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes Lamin A, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side of the removed sequence being joined together.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western"), and affinity chromatography. Examples of useful epitope tags include FLAG, T7, HA (hemagglutinin) and myc. The FLAG tag (DYKDDDDK) was used in some particular examples disclosed herein because high quality reagents are available to be used for its detection.

Genomic target sequence: A sequence of nucleotides located in a particular region in the human genome that corresponds to one or more specific genetic abnormalities, such as a nucleotide polymorphism, a deletion, or an amplification. The target can be for instance a coding sequence; it can also be the non-coding strand that corresponds to a coding sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence. For example, an oligonucleotide can be complementary to a Lamin A encoding mRNA, or a Lamin A-encoding dsDNA.

"Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when binding of the oligonucleotide or analog to the target DNA or RNA molecule interferes with the normal function of the target DNA or RNA, and there is a sufficient degree of complementarity to avoid non-specific binding of the oligonucleotide or analog to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ concentration) of the hybridization buffer will determine the stringency of hybridization, though waste times also influence stringency. Calculations regarding hybridization conditions required for attaining particular degrees of stringency are discussed by Sambrook et al. (ed.), *Molecular Cloning: A Laboratory Manual*, 2nd ed., vol. 1-3, Cold Spring Harbor Laboratory Press, Cold Spring Harbor, N.Y., 1989, chapters 9 and 11, herein incorporated by reference.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize.

Isolated: An "isolated" biological component (such as a nucleic acid molecule, protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Open reading frame: A series of nucleotide triplets (codons) coding for amino acids without any internal termination codons. These sequences are usually translatable into a peptide.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Peptide Nucleic Acid (PNA): An oligonucleotide analog with a backbone comprised of monomers coupled by amide (peptide) bonds, such as amino acid monomers joined by peptide bonds.

Pharmaceutically acceptable carriers: The pharmaceutically acceptable carriers useful with this disclosure are conventional. Martin, *Remington's Pharmaceutical Sciences*, published by Mack Publishing Co., Easton, Pa., 19th Edition, 1995, describes compositions and formulations suitable for pharmaceutical delivery of the nucleotides and proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polymorphism: Variant in a sequence of a gene. Polymorphisms can be those variations (nucleotide sequence differences) that, while having a different nucleotide sequence, produce functionally equivalent gene products, such as those variations generally found between individuals, different ethnic groups, geographic locations. The term polymorphism also encompasses variations that produce gene products with altered function, e.g., variants in the gene sequence that lead to gene products that are not functionally equivalent. This term also encompasses variations that produce no gene product, an inactive gene product, or increased gene product. The term polymorphism may be used interchangeably with allele or mutation, unless context clearly dictates otherwise.

Polymorphisms can be referred to, for instance, by the nucleotide position at which the variation exists, by the change in amino acid sequence caused by the nucleotide variation, or by a change in some other characteristic of the nucleic acid molecule that is linked to the variation (e.g., an alteration of a secondary structure such as a stem-loop, or an alteration of the binding affinity of the nucleic acid for associated molecules, such as polymerases, RNases, and so forth). In the current instance, Mutation 1 is also referred to as G608G(GGC>GGT), indicating that the mutation is in codon 608, that it is silent (in that it causes no change in the encoded amino acid), and that the exact nucleotide sequence change is C to T in the third position of the codon. Similarly, Mutation 2 is also referred to as G608S(GGC>AGC), indicating that the mutation is in codon 608, that it causes an amino acid substitution (glycine to serine), and that the exact nucleotide sequence change is G to A in the first position of the codon.

Probes and primers: A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual*, CSHL, New York, 1989) and Ausubel et al. (In *Current Protocols in Molecular Biology*, John Wiley & Sons, New York, 1998).

Primers are short nucleic acid molecules, for instance DNA oligonucleotides 10 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic-acid amplification methods known in the art. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Nucleic acid probes and primers can be readily prepared based on the nucleic acid molecules provided in this disclosure. It is also appropriate to generate probes and primers based on fragments or portions of these disclosed nucleic acid molecules, for instance regions that encompass the identified polymorphisms at nucleotide 1822 and nucleotide 1824 within the LMNA coding sequence.

Methods for preparing and using nucleic acid probes and primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). Amplification primer pairs can be derived from a known sequence, for example, by using computer programs intended for that purpose such as Primer (Version 0.5 © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of a Lamin A-encoding nucleotide or flanking region thereof (a "Lamin A primer" or "Lamin A probe") will anneal to a target sequence with a higher specificity than a corresponding primer of only 15 nucleotides. Thus, in order to obtain greater specificity, probes and primers can be selected that comprise at least 20, 25, 30, 35, 40, 45, 50 or more consecutive nucleotides of a Lamin A nucleotide sequence.

The disclosure thus includes isolated nucleic acid molecules that comprise specified lengths of the Lamin A encoding sequence and/or flanking regions. Such molecules may comprise at least 10, 15, 20, 23, 25, 30, 35, 40, 45 or 50 consecutive nucleotides of these sequences or more, and may be obtained from any region of the disclosed sequences. By way of example, the human LMNA locus, cDNA, ORF, coding sequence and gene sequences (including sequences both upstream and downstream of the LMNA coding sequence) may be apportioned into about halves or quarters based on sequence length, and the isolated nucleic acid molecules (e.g., oligonucleotides) may be derived from the first or second halves of the molecules, or any of the four quarters. The cDNA also could be divided into smaller regions, e.g. about eighths, sixteenths, twentieths, fiftieths and so forth, with similar effect.

In particular embodiments, isolated nucleic acid molecules comprise or overlap at least one residue position designated as being associated with a polymorphism that is predictive of progeria and/or a premature aging disease or condition. Such polymorphism sites include position 1822 (corresponding to the Mutation 2 polymorphism) and position 1824 (corresponding to the Mutation 1 polymorphism).

Protein: A biological molecule, particularly a polypeptide, expressed by a gene and comprised of amino acids.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Representational difference analysis: A PCR-based subtractive hybridization technique used to identify differences in the mRNA transcripts present in closely related cell lines.

Serial analysis of gene expression: The use of short diagnostic sequence tags to allow the quantitative and simultaneous analysis of a large number of transcripts in tissue, as described in Velculescu et al. (*Science* 270:484-487, 1995).

Specific binding agent: An agent that binds substantially only to a defined target. Thus a Lamin A protein-specific binding agent binds substantially only the Lamin A protein. As used herein, the term "Lamin protein specific binding agent" includes anti-Lamin protein antibodies (and functional fragments thereof) and other agents (such as soluble receptors) that bind substantially only to a Lamin protein. It is particularly contemplated in specific embodiments that certain Lamin-specific binding agents are specific for one form of Lamin, such as Lamin A or Lamin C.

Anti-Lamin protein antibodies may be produced using standard procedures described in a number of texts, including Harlow and Lane (*Antibodies, A Laboratory Manual*, CSHL, New York, 1988). The determination that a particular agent binds substantially only to the target protein may readily be made by using or adapting routine procedures. One suitable in vitro assay makes use of the Western blotting procedure (described in many standard texts, including Harlow and Lane (*Antibodies, A Laboratory Manual*, CSHL, New York, 1988)). Western blotting may be used to determine that a given target protein binding agent, such as an anti-Lamin A protein monoclonal antibody, binds substantially only to the specified target protein.

Shorter fragments of antibodies can also serve as specific binding agents. For instance, FAbs, Fvs, and single-chain Fvs (SCFvs) that bind to Lamin A would be Lamin A-specific binding agents. These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb')2, the fragment of the antibody obtained by treating whole antibody with the enzyme pepsin without subsequent reduction; (4) F(Ab')2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

Subject: Living multi-cellular vertebrate organisms, a category that includes both human and non-human mammals. This term encompasses both known and unknown individuals, such that there is no requirement that a person working with a sample from a subject know who the subject is, or even from where the sample was acquired.

Target sequence: "Target sequence" is a portion of ssDNA, dsDNA or RNA that, upon hybridization to a therapeutically effective oligonucleotide or oligonucleotide analog, results in the inhibition of expression. For example, hybridization of a therapeutically effective oligonucleotide to an LMNA target sequence results in inhibition of Lamin A expression. Either an antisense or a sense molecule can be used to target a portion of dsDNA, since both will interfere with the expression of that portion of the dsDNA. The antisense molecule can bind to the plus strand, and the sense molecule can bind to the minus strand. Thus, target sequences can be ssDNA, dsDNA, and RNA.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Hutchinson-Gilford Progeria Syndrome

Hutchinson-Gilford Progeria Syndrome (HGPS, OMIM #176670) is an extremely rare premature aging syndrome affecting approximately one in 8 million live births (DeBusk, *J. Pediat.* 80:697-724, 1972). This disorder is also commonly referred to as "progeria," or "progeria of childhood". The clinical features are remarkably reproducible. Typically affected children appear normal at birth, but within a year the characteristic features of failure to thrive, delayed dentition, alopecia, and sclerodermatous skin changes begin to appear. Children typically exhibit normal intelligence, very short stature, poor weight gain, and incomplete sexual maturation. Death occurs on average at age 13, and at least 90% of the patients die from progressive atherosclerosis of the coronary and cerebrovascular arteries (Baker et al., *Arch. Pathol. Lab. Med.* 105:384-386, 1981; Shozawa et al., *Acta Pathol. Jpn.* 34:797-811, 1984). Though commonly referred to as a premature aging syndrome, some of the features of the normal aging process (such as cataracts, Alzheimer's disease, and presbyopia) are not observed in patients with HGPS.

The inheritance pattern has not previously been known, since nearly all cases appear sporadic. In favor of a sporadic dominant mutation as the cause are reports of a modest paternal age effect, the paucity of affected sibpairs (even in very large sibships), and the limited reports of known consanguinity (Jones et al., *J. Pediatr.* 86:84-88, 1975; Brown, *Mech. Aging. Dev.* 9:325-336, 1979; and Brown et al., "Progeria: a genetic disease model of premature aging." In *Genetic Effects on Aging II* (ed. Harrison, D. E.) 521-542, The Telford Press, Inc., Caldwell, N.J., 1990). It is believed that the known consanguinity rate does not exceed the rate in the general population. In favor of a recessive mutation are the rare reports of affected sibpairs (Franklyn, *Clin. Radiol.* 27:327-333, 1976; Trevas-Maciel, *Am. J. Med. Genet.* 31:483-487, 1988; Khalifa, *Clin. Genet.* 35:125-132, 1989; Parkash et al., *Am. J. Med. Genet.* 36:431-433, 1990), though some have argued that those cases do not represent classic Progeria, but are rather instances of a related disease such as mandibuloacral dysplasia (Schrander-Stumpel et al., *Am. J. Med. Genet.* 43:877-881, 1992).

IV. Lamin A

Lamins, members of the intermediate filament family of proteins, are components of the nuclear lamina, a fibrous layer on the nucleoplasmic side of the inner nuclear membrane, which is thought to provide a framework for the nuclear envelope and may also interact with chromatin. Lamin A and C are present in roughly equal amounts in the lamina of mammals. Lamin A/C are products of the same locus, LMNA, and are generated by alternative splicing of the same original transcript. Lamin A consists of exons 1-12, while Lamin C consists of exons 1-10. A splice site within exon 10, which is upstream of the stop codon for Lamin C, splices together with exon 11 in Lamin A. The last six amino acids of Lamin C are not present in Lamin A.

As illustrated in FIG. 5, part of exon 1 of LMNA encodes the N-terminal globular domain, the rest of exon 1 through to part of exon 7 encodes the central helical domain, and the rest of exon 7 to 12 encodes the C-terminus of lamin A. Lamin C has a similar structure, but is shorter at the C-terminus, which is encoded by exons 7 to 10. The elongated C-terminus of lamin A bears a terminal tetrapeptide sequence known as the CaaX (SEQ ID NO: 66) motif (where C is cysteine, "a" is any amino acid bearing an aliphatic side-chain and X is any amino acid). This motif is the site of post-translational addition of a hydrophobic isoprene (farnesyl) group, which allows it to be incorporated into the inner nuclear membrane. Following membrane localization, the CaaX (SEQ ID NO: 66) motif and its contiguous 18 residues are removed by proteolytic cleavage, yielding the mature form of lamin A. The shorter C-terminus of lamin C does not undergo these post-translational modifications and its integration into the inner nuclear membrane is dependent upon association with lamin A.

The structural integrity of the lamina is strictly controlled by the cell cycle, as seen by the disintegration and formation of the nuclear envelope in prophase and telophase, respectively. Increased phosphorylation of the lamins occurs before envelope disintegration and probably plays a role in regulating lamin associations.

V. Disease Previously Linked to Lamin A/C

Defects in LMNA are a cause of Emery-Dreifuss muscular dystrophy (EDMD; e.g., associated with heterozygous R527P), an autosomal recessive or dominant disease characterized by muscle weakness, contractures, and cardiomyopathy with conduction defects. In addition, defects in LMNA are a cause of dilated cardiomyopathy 1a (CMD1A; e.g., associated with R644C). Further, defects in LMNA are a cause of familial partial lipodystrophy (Dunnigan variety) (FPLD), an autosomal dominant disorder characterized by marked loss of subcutaneous adipose tissue from the extremities and trunk but by excess fat deposition in the head and neck. This condition is frequently associated with profound insulin resistance, dyslipidemia, and diabetes. Very recently specific mutations in LMNA have been identified in patients with the recessive disease mandibuloacral dysplasia (e.g., associated with homozygous R527H).

VI. The Involvement of Lamin A in HGPS, Arteriosclerosis and Aging

Surprisingly, point mutations have been identified in the LMNA gene that cause HGPS. The inheritance is new mutation autosomal dominant, and identified mutations occur in codon 608; the most common is due to a C to T base substitution in a CpG dinucleotide. It is currently believed that the mechanism of the mutations is activation of a cryptic splice site within the LMNA gene, which leads to deletion of part of exon 11 and generation of a Lamin A protein product that is 50 amino acids shorter than the normal protein. All of the identified mutations are predicted to affect Lamin A but not Lamin C. In addition, two cases of classical HGPS that were identified with segmental UPD of chromosome 1q from fibroblast DNA do not show the mutation, which may be indicative of a (in vivo or in vitro) somatic rescue event.

The results described herein can be generalized to the aging process and related conditions and diseases, beyond progeroid diseases. This is because HGPS is in many respects closely connected to normal aging processes. HGPS continues to be recognized as a useful model of aging (Fossel, *Human aging and progeria. J Pediatr Endocrinol Metab.* 13 Suppl 6:1477-1481, 2000). For instance, the connection to atherosclerosis is very strong, especially of the coronary arteries. In addition, alopecia in HGPS is similar to that seen in subjects with advanced age. Further, the prime cellular feature of HGPS, as described many years ago by Hayflick and others (Hayflick, *The cell biology of human aging. N Engl J Med* 295:1302-1308, 1976) is early cellular senescence. The limited number of cell divisions in HGPS fibroblasts is similar to what is seen in fibroblasts derived from elderly individuals. That was further explored recently by research showing similarities in the gene expression patterns of HGPS fibroblasts and those derived from elderly persons, distinguishing them from fibroblasts derived from younger persons (Ly et al., *Science* 287: 2486-2492, 2000).

Specific Identified Mutations

The more common change identified (referred to herein as Mutation 1) is at nucleotide position 4277 in GI 292250 (accession number L12401), which corresponds to amino acid 608 in accession number P02545; this mutation does not change the amino acid-sequence but rather is predicted to generate a cryptic splice site that leads to an alternative splicing variant of Lamin A. In Mutation 2 there is a change at nucleotide position 4275 in GI 292250, which corresponds to amino acid 608; this mutation changes a glycine to a serine in Lamin A, and is predicted to generate the same cryptic splice site as mutation 1. Hence both Mutation 1 and Mutation 2 generate the same mutant Lamin A protein. The two mutations both occur in the same codon, which encodes amino acid 608.

The discovery that rare variants in the sequence of LMNA cause HGPS also enables a variety of diagnostic, prognostic, and therapeutic methods that are further embodiments. The new appreciation of the role of Lamin A in HGPS and more generally aging illnesses and arteriosclerosis/atherosclerosis enables detection of predisposition to these conditions in a subject. This disclosure also enables early detection of subjects at high risk of these conditions, and provides opportunities for prevention and/or early treatment.

Since it is predicted that Mutations 1 and 2 will produce a protein that is 50 amino acids shorter than the wild type Lamin A, a convenient diagnostic method to identify HGPS is to perform a Western blot and look for the abnormal (shorter) band.

In addition, the deletion of the last half of exon 11 (as is predicted to occur with mutations 1 and 2) removes a cleavage site that is normally necessary for processing of Lamin A. The CaaX box at the C-terminus of Lamin A, which is still present in the mutant forms, allows anchoring of the protein in the membrane—but then this anchoring mechanism is normally removed by the processing cleavage. The Lamin A mutant protein described herein is predicted not to be cleaved, and thus may be trapped in this membrane location. Since Lamin A is part of a large multiprotein complex, its mislocalization may well pull other bystander proteins into the same improper location. It is possible that this will lead to structural abnormalities of the nucleus that could be diagnostic for HGPS, and which could be visualized by light microscopy, immunohistochemistry, immunofluorescence, confocal microscopy, or electron microscopy.

Not meaning to be limited to a single mechanism, it is currently believed that mutations in LMNA that cause HGPS will always be dominant.

It is now believed that the uniparental isodisomy seen in some HGPS patients, including ones described herein, was by a remarkable and rather unprecedented mechanism. It is believed, for instance, that at the time of conception individual C8803 had the common G608G mutation described herein. But, as shown by decades of work on skin fibroblasts from subjects with HGPS, cells from individuals with this disease grow less well than normal ones. We postulate that, either in vivo in the patient, or in vitro in the cell culture, a rare mitotic crossing over event occurred, leading to a cell that had lost the long arm of chromosome 1 that contained the G608G mutation, and instead duplicated the normal arm of chromosome 1. That rare event would have essentially "cured" the cell of HGPS, and those cells would then grow better than their neighbors. Ultimately, in the cell culture that was studied, none of the original mutant cells remained, only the rescued cells. This explains why the two patients with UPD, and the one with a deletion (which may also have been a "somatic rescue" event) are the only ones that do not show a mutation in Table 2. Based on this explanation, it is believed that an agent that promotes mitotic crossing over may be beneficial in treating HGPS, if given early enough. Essentially such a drug would inspire self-healing on a cell-by-cell basis.

The following examples are provided to illustrate certain particular features and/or embodiments. These examples should not be construed to limit the invention to the particular features or embodiments described.

EXAMPLES

Example 1

Identification of LMNA as Implicated in HGPS

This example provides evidence of rare sequence variants in LMNA that are linked to and causative for Hutchinson-Gilford Progeria Syndrome (HGPS, OMIM #176670), based on molecular genetic analysis of patients with this disorder.

HGPS is an extremely rare progeroid syndrome. Death occurs on average at age 16, usually from cardiovascular disease. The inheritance pattern of HGPS is not known. The presence of very few reported affected sibpairs and a modest paternal age effect, together with very few cases of known consanguinity, has led some to favor a sporadic dominant mechanism. However, a previous report of a consanguineous family with four affected siblings favored autosomal recessive inheritance.

This example demonstrates that de novo mutations in lamin A are the cause of this disorder. Initially the HGPS gene was localized to chromosome 1q by observing two cases of uniparental isodisomy of 1q, and one case with a six megabase (6 Mb) interstitial deletion of all paternal alleles. Lamin A (LMNA) maps within this interval and emerged as an attractive candidate gene, particularly in view of its role in a number of other potentially related heritable conditions. Sequencing LMNA in 20 classic cases of HGPS revealed that 18 of them harbored exactly the same single base substitution, G608G(GGC>GGT), within exon 11 of this gene. The mutation was not found in the parents of the affected children, indicating that in each case it arose de novo. One additional case was identified with a different substitution within the same codon [G608S(GGC>AGC)]. Both of these mutations were shown to result in activation of a cryptic splice site within exon 11, resulting in production of a transcript that deletes 50 amino acids near the C-terminus. Western blotting confirmed the presence of an abnormal protein product, and immunofluorescence of HGPS fibroblasts with antibodies directed against lamin A revealed that many cells show visible abnormalities of the nuclear membrane. Without intending to be limited to a single possible explanation, it is currently believed that the abnormal lamin A protein acts as a dominant negative, resulting in nuclear membrane instability that may be particularly critical in tissues subjected to mechanical shearing. The discovery of the molecular basis of this model of premature aging will shed light on the general phenomenon of human aging.

Methods and Materials

Subjects and DNA/RNA Preparation

This study was approved through the NIH Human Subjects review process. Primary dermal fibroblast cell cultures and EBV transformed lymphoblastoid cell lines from individuals diagnosed as classical HGPS and their first degree relatives (when available), were obtained from the Aging Repository of the Coriell Cell Repository (CCR), Camden, N.J., and the Progeria Research Foundation Cell and Tissue Bank, Peabody, Mass. DNA was prepared using the Puregene DNA isolation kit (Gentra Systems, Minneapolis, Minn.). The genome scan for homozygosity included samples derived from 12 classical HGPS patients (samples AG01972, AG03259, AG03344, AG03506, AG06297, AG06917, AG10578, AG10579, AG10587, AG10801, AG11498, and AG11513) and 16 unaffected first degree relatives (samples AG03258, AG03260, AG03262, AG03263, AG03343, AG03342, AG03345, AG03346, AG03504, AG03505, AG03507, AG03508, AG06298, AG06299, AG10585, AG10588). Additional samples used in this study were samples from classical HGPS (samples AG10677, HGADFN001, HGADFN003, HGALBV009, HGALBV011, HGALBV057, HGADFN005, HGADFN008, HGADFN014, HGALBV071, C8803 [also known as AG10548 in the CCR]) and samples derived from their unaffected first degree relatives (samples HGMLBV010, HGFLBV021, HGMLBV023, HGFLBV031, HGMLBV066, HGFLBV067, HGMLBV013, HGFLBV050, HGMLBV058, HGSLBV059, HGMLBV078, HGFLBV079, HGFLBV082, and HGMLBV081). Total RNA was extracted from cells with TRIzol reagent (Invitrogen).

Genotyping

The whole genome scan included 403 highly polymorphic microsatellite markers with an average spacing of 9.2 cM and average heterozygosity of ~0.8 (Gillanders et al. manuscript in preparation). Pedigree checking was performed using Ped-Check (O'Connell & Weeks, *Am J Hum Genet* 63:259-266, 1998) and any identified genotype errors were removed. We carried out homozygosity mapping assuming various degrees of inbreeding for the HGPS cases (Smith, J. R. *Stat. Soc. B* 15:153-184, 1953). Additional microsatellite repeats on chromosome 1q were identified using the Sputnik program (Abajian, 1994; program available on-line from the University of Washington Department of Molecular Biotechnology) (Table 1) and were used to further investigate the UPD cases and the paternal deletion region in C8803. Microsatellite markers were analyzed using a 3100 genetic analyzer (PE Biosystems). Genotypes were analyzed using GeneScan 3.7 and Genotyper 2.5 Software (PE Biosystems).

TABLE 1

Microsatellite markers chromosome 1q21.3-23.1

| Marker name | Forward primer (SEQ ID NO) | Reverse primer (SEQ ID NO) | Het | UCSC June 2002 | CEPH 1347-02 |
|---|---|---|---|---|---|
| Pdi3 | 8 | 33 | 0.81 | 151044102 | 214/220 |
| Ptetra4 | 9 | 34 | 0.43 | 151052373 | 284/300 |
| Pdi5 | 10 | 35 | 0.17 | 151065623 | 209/209 |
| Pdi9 | 11 | 36 | 0.56 | 151100876 | 240/240 |
| Pdi10 | 12 | 37 | 0.55 | 151113665 | 277/281 |
| Ptetra11 | 13 | 38 | 0.53 | 151124124 | 328/340 |
| Pdi12 | 14 | 39 | 0.56 | 151124433 | 178/182 |
| Ptetra13 | 15 | 40 | 0.74 | 151052373 | 336/380 |
| Ptetra16 | 16 | 41 | 0.86 | 151229282 | 182/186 |
| Ptri25 | 17 | 42 | 0.53 | 151484881 | 167/167 |
| Pdi36 | 18 | 43 | 0.73 | 151564908 | 187/187 |
| Pdi74 | 19 | 44 | 0.76 | 152144879 | 259/275 |
| Pdi119 | 20 | 45 | 0.6 | 152774348 | 176/176 |
| Dtri22 | 21 | 46 | 0.39 | 156340181 | 177/177 |
| Ddi24 | 22 | 47 | 0.84 | 156372998 | 260/266 |
| Ddi30 | 23 | 48 | 0.75 | 156475805 | 239/239 |
| Dtetra32 | 24 | 49 | 0.72 | 156485165 | 115/115 |
| Dtetra39 | 25 | 50 | 0.35 | 156607074 | 314/314 |
| Dtetra43 | 26 | 51 | 0.22 | 156669559 | 286/286 |
| Dtetra46 | 27 | 52 | 0.74 | 156708500 | 236/236 |
| Ddi47 | 28 | 53 | 0.49 | 156735453 | 232/238 |
| Ddi51 | 29 | 54 | 0.24 | 156782785 | 300/300 |
| Ddi59 | 30 | 55 | 0.49 | 156890236 | 131/135 |
| Ddi60 | 31 | 56 | 0.62 | 156892710 | 158/162 |
| Ddi62 | 32 | 57 | 0.6 | 156905327 | 246/256 |

Fish

Single-color and two-color FISH was performed on metaphases from sample C8803 following previously published procedures (Casper et al., *Cell* 111:779-789, 2002), using a subset of BACs in the region of the paternal deletion. BACs used as probes for the FISH analysis were RP1-140J1, RP1-148L21, RP1-178F15, RP11-137P24, RP11-66D17, RP11-110J1, RP11-91G5, RP11-120D12, RP11-101J8, RP11-81N17, RP11-144L1, RP11-317F9, RP11-452022, and RP11-137M19.

Mutation Analysis of LMNA

Direct sequencing of LMNA was performed primarily using previously described primer sequences for the LMNA exons 1-12 (De Sandre-Giovannoli et al., *Am. J. Hum. Genet.* 70:726-736, 2002). Additional primers for LMNA were designed for three exons: exon 4 (5'-agcactcagctcccaggtta-3' and 5'-ctgatcccagaaggcatag-3'; SEQ ID NOs: 58 and 59), exon 6 (5'-gtccctccttccccatactt-3' and 5'-ccaagtgggggtctagtcaa-3'; SEQ ID NOs: 60 and 61), and exon 7 (5'-aggtgctg-gcagtgtcctct-3' and 5'-ctctgagggcaaggatgttc-3'; SEQ ID NOs: 62 and 63). All primers used for sequencing were synthesized with M13 forward and reverse tags. The PCR products were cleaned up with the QiaQuick PCR purification kits using the BioRobot 8000 Automated Nucleic Acid Purification and Liquid Handling robot (Qiagen). Sequencing reactions were performed at quarter strength reaction volumes with the Big Dye Terminator chemistry kit (Applied Biosystems), and electrophoresed on an ABI 3700 DNA Analyzer (Applied Biosystems). Multiple sequence alignment was performed with Sequencher (Genecodes Inc., Ann Arbor, Mich.). Attempts were made to sequence all PCR products in both directions, but approximately 13% of exons failed to yield readable sequence.

RT-PCR on Exon 11

For all RNA samples, 20 μg of total RNA was treated with RQ1 RNase-Free DNase according to manufacturer's recommendations (Promega, USA). 800 ng of DNase-treated total RNA was used for first strand cDNA synthesis with random hexamers (Superscript™, Invitrogen). Control samples without reverse transcriptase were processed at the same time for each sample. PCR primers for the lamin A/C gene were designed in exon 7/8 and exon 12. Primer sequences were 5'-gcaacaagtccaatgaggacca-3' and 5'-gtcccagattacatgatgc-3' (SEQ ID NOs: 64 and 65). PCR fragments were gel-purified or cloned (TOPO TA-cloning kit, Invitrogen) and sequenced. PCR with GAPDH-specific primers were performed on all samples as control.

Western Analysis

Whole cells ($1\times10^6$) were harvested and washed 2× in PBS. The pellets were resuspended in RIPA buffer (50 mM Hepes pH 7, 0.1% SDS, 1% Triton X-100, 1 mM EDTA, 1% Deoxycholic acid, and 150 mM NaCl), including a cocktail of proteinase inhibitors (Roche). Protein concentrations were assayed with the BCA protein assay kit (Pierce, Perbio, Rockford, USA) and analyzed on a spectrophotometer. Twenty μg of protein was mixed with SDS protein-loading buffer, boiled for two minutes and placed on ice, and then electrophoresed on an 8% Tris-Glycine mini gel (Invitrogen). Blots were transferred to nitrocellulose and incubated with primary monoclonal antibody against lamin A/C (JOL2, Chemicon International, USA) at 4° C., for 12 hours. Following room temperature washes in TBST, FITC-conjugated secondary antibody (Jackson ImmunoResearch laboratories, USA) was added and incubated for 45 minutes at room temperature. The filters were exposed using the ECL+ plus Western blotting detection system (Amersham Biosciences).

Immunofluorescence

Fibroblasts were cultivated on cover slips in 24-well dishes at 37° C. in the presence of 5% $CO_2$. Cells at 50-70% confluence were fixed (3.2% PFA), permeabilized (1% NP40), and blocked (0.1% Brij58, and 5% goat or donkey serum corresponding to $2^{nd}$ antibody origin). Lamin A/C (monoclonal antibodies JOL2, Chemicon International, USA, and clone XB10, CRP Inc., USA) and mitochondria (HMS-0100, Immunovision Inc., Springdale, Ala., USA) were labeled for immunofluorescence. For staining of nuclear DNA, 4,6-diamidine-2-phenylindole dihydrochloride (DAPI) was added during the incubation with the $2^{nd}$ antibody at 1 μg/ml. Analysis was done by confocal microscopy using a BioRad 1024 and Leica SP2 system, and visualized as green (lamin A/C), red (mitochondria), and blue (DAPI) color channels using CoolLocalizer imaging software (Cytolight, Stockholm, Sweden).

Cell Cycle and Apoptosis

Cells were harvested and washed in PBS, one day following the immunofluorescence experiments. Duplicate experiments were performed on each cell culture. A total of 5×10⁵ cells were resuspended in 0.5 ml of NuCycl Propidium Iodide (NuCycl™ PI kit, Exalpha Corp., Boston, Mass.) and processed as recommended by the manufacturer. The total DNA content was measured by DNA flow cytometry. Cells were also assayed for viability using Annexin V-FITC and Propidium Iodide according to standardized procedures (BD Biosciences).

Results

Initial Mapping of the HGPS Gene to Chromosome 1q

Figure 1A:
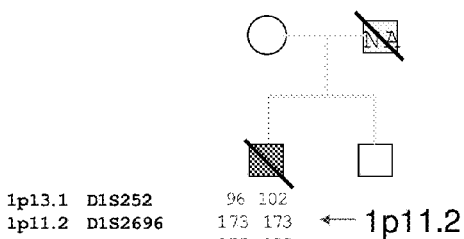
FIG. 1A shows a marker comparison between two HGPS cases that were identified with segmental uniparental isodisomy (UPD) of chromosome 1q. A subset of markers and their genotypes are shown. More than 100 chromosome 1q specific microsatellite markers have been analyzed, with an average spacing of 1.75 cM. As illustrated, every marker on the q arm between at least marker 1q22 and marker 1q44 showed homozygosity. SKY and G-banding showed a normal karyotype for these individuals and there were no other regions of homozygosity on the other chromosomes which rules out the possibility of consanguinity. NA indicates sample not available.
Figure 1A:
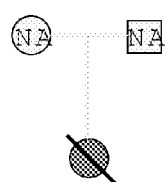

A genome-wide scan searching for evidence of homozygosity was conducted, a powerful tool to identify loci for rare recessive disorders (Smith, *J. R. Stat. Soc. B* 15:153-184, 1953; Lander & Botstein, *Science* 236:1567-1570, 1987). Assuming that in a rare recessive disorder, many cases will be homozygous for a particular mutation, one would expect to see statistical evidence for homozygosity of closely linked markers in the region of the gene. A whole genome scan including 403 polymorphic microsatellite markers with an average spacing of 9.2 cM was performed on 12 DNA samples derived from individuals considered to represent classic HGPS. While no evidence of homozygosity was identified in the overall sample set, two HGPS samples were found to have uniparental isodisomy (UPD) of chromosome 1q (FIG. 1A). For one of these cases, DNA samples from the mother and the brother were available. In that case, it was possible to determine that the isodisomic segment is of maternal origin, and that there is biparental inheritance of the short arm of chromosome 1. Spectral karyotyping (SKY) and G-banding of one of the two UPD cases showed a normal karyotype.

Figure 1B:
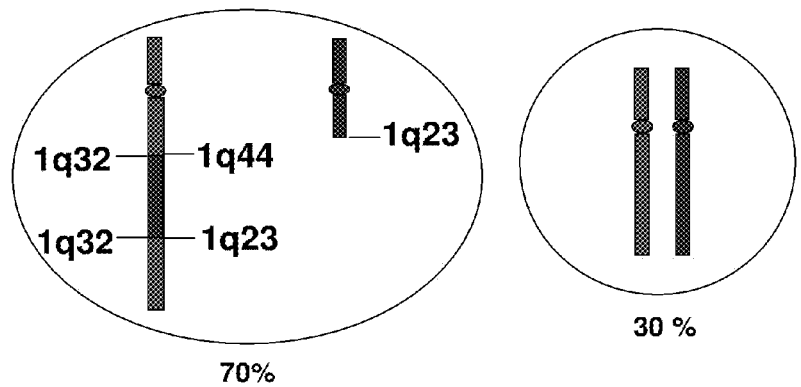
FIG. 1B is the karyotype described by Brown et al. (ASHG Abstract, 1990), which illustrates the karyotyping of an individual (sample C8803) with a more severe form of HGPS. The subject was mosaic for a balanced inverted insertion on chromosome 1q.
Figure 1C:
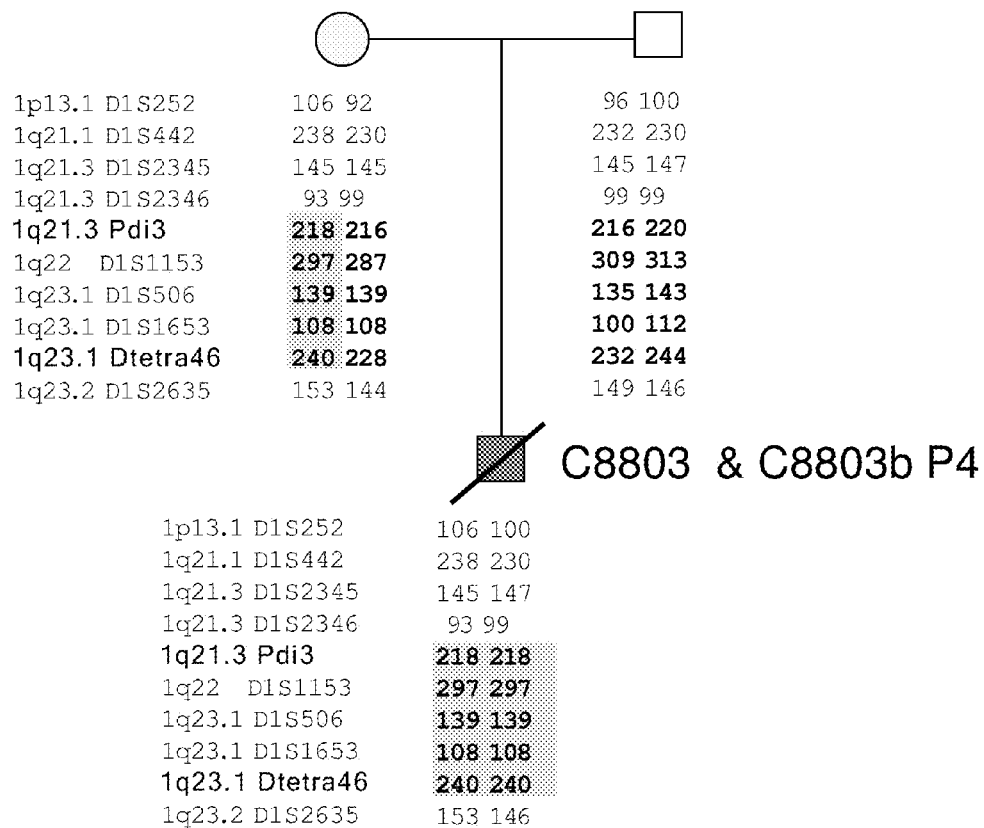
FIG. 1C illustrates the genotyping pedigree for proband C8803 (another sample ID for this patient is AG10548), which showed a paternal deletion of approximately 6 Mb between 1q21.3 and 1q23.1. A subset of informative markers and their genotypes in the region of the paternal deletion are shown. The boxed interval is the region that has been inherited exclusively from the mother. Though the sample was mosaic for a chromosome rearrangement (earlier reported by T. Brown et al., ASHG Abstract, 1990), the deletion appeared to affect 100% of the cells.
Figure 1D:
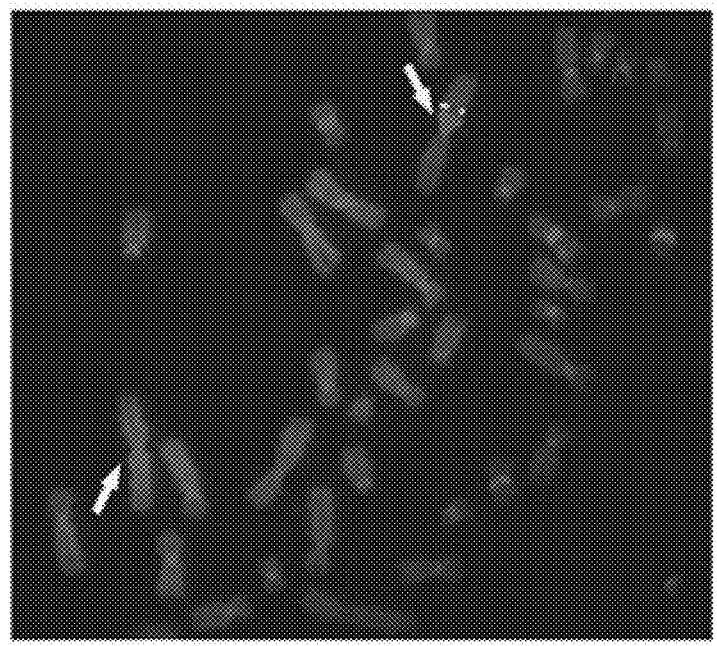
FIG. 1D shows a FISH hybridization analysis of a metaphase spread from C8803 fibroblasts, using a BAC probe within the deletion interval. This metaphase is from one of the cells in the mosaic sample that was supposedly karyotypically normal, but it clearly shows complete deletion of the BAC signal on one of the chromosomes 1.
Figure 1E:
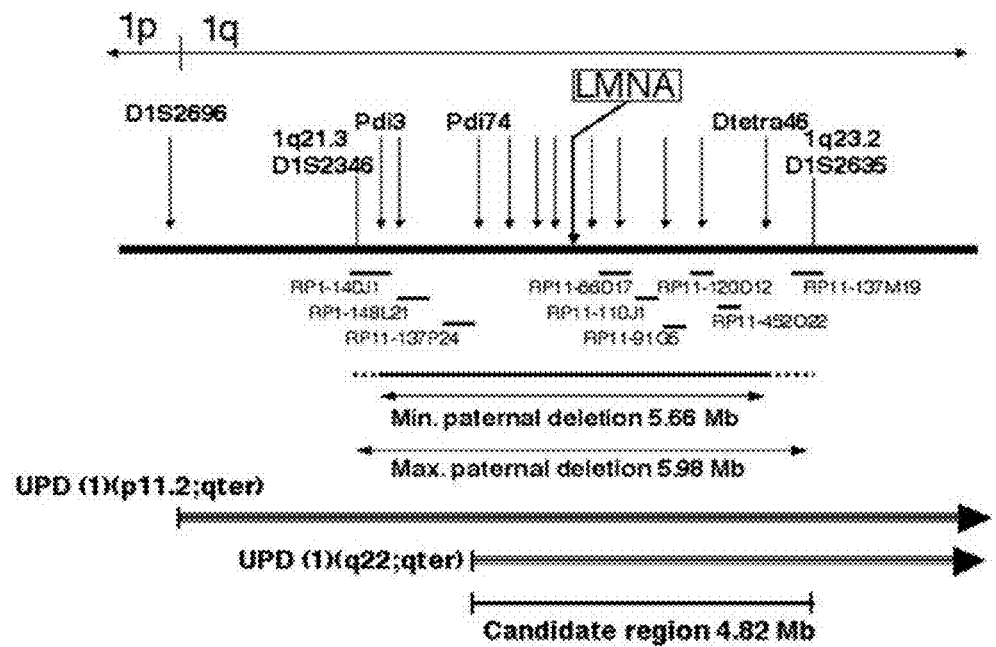
FIG. 1E is a map of the paternal deletion region on 1q21.3-q23.2, observed in sample C8803. Microsatellite markers are indicated with arrows; the markers that define the maximal deletion region in C8803 are D1S2346 and D1S2635. The thick short horizontal lines indicate BAC probes that were used for FISH on sample C8803. RP1-140J1 and RP11-137M19 fall outside the deletion region, whereas the other BACs are within it. Combining the information from this deletion with the boundary of one of the cases of UPD, the candidate interval for the HGPS gene can be delimited to 4.82 Mb. LMNA is one of the ~80 known genes in this interval.

An earlier report (Brown, *Am. J. Clin. Nutr.* 55:1222 S-1224S, 1992) described an abnormal karyotype in a monozygotic twin with HGPS. That report described a mosaic cell population in which 70% of the cells contained a balanced inverted insertion [46 XY, inv ins (1;1)(q32; q44q23)], whereas the rest of the cells had an apparently normal karyotype. A fibroblast culture was obtained from the same individual (sample ID C8803), as well as his parents. Karyotyping confirmed the original result, though only a small minority of the metaphases now showed the rearrangement of chromosome 1 (FIG. 1B). Surprisingly, genotyping of microsatellite markers identified a roughly 6 megabase interval where all paternal markers were completely missing (FIG. 1C). It was confirmed that this deletion was also present in the cells that had an apparently normal karyotype, using fluorescent in situ hybridization (FISH) with BACs that map throughout this interval (FIG. 1D). Putting all of this information together with genotypes from a total of 44 additional microsatellite markers, it was determined that the HGPS gene must lie in an interval of 4.82 Mb on proximal chromosome 1q (FIG. 1E).

Identification of the HGPS Gene

The candidate interval contains roughly 80 known genes. Attention was drawn to one of them, the LMNA gene that encodes two protein products (Lamin A and Lamin C), representing major constituents of the inner nuclear membrane lamina. Mutations in LMNA have previously been found to be the cause of six different recessive and dominant disorders, including Emery-Dreifuss muscular dystrophy type 2, a form of dilated cardiomyopathy, the Dunnigan type of familial partial lipodystrophy, limb girdle muscular dystrophy type 1B, Charcot-Marie-Tooth disorder type 2B1, and mandibuloacral dysplasia (for a review of laminopathies, see Burke & Stewart, *Nature Rev.* 3:575-585, 2002).

The LMNA gene contains 12 exons and covers ~25 kb of genomic DNA. Lamin A is coded by exons 1-12 and lamin C by exons 1-10 (FIG. 5). A splice site within exon 10, located just upstream of the stop codon for lamin C, splices together with exons 11 and 12 to code for lamin A (McKeon et al., *Nature* 319:463-468, 1986; Fisher et al., *Proc. Nat. Acad. Sci.* 83:6450-6454, 1986; Lin & Worman, *J. Biol. Chem.* 268: 16321-16326, 1993).

PCR amplification of all of the exons of the LMNA gene (including exon-intron boundaries), followed by direct sequencing, was carried out in 23 samples from patients with classical HGPS. In 18 of these samples, a heterozygous base substitution [G608G(GGC>GGT)] within exon 11 of the LMNA gene was identified (FIG. 2A). In HGPS sample AG10801 a different heterozygous base substitution was identified within the same codon [G608S(GGC>AGC)] (FIG. 2A). In HGPS sample AG10677, a heterozygous base substitution was identified within exon 2 [E145K (GAG>AAG)].

In the eight cases where DNA from both parents was available, the G608G mutation was absent in the parents, confirming that these are de novo mutations. Similarly, the G608S and E145K mutations were not found in parents of AG10801 or AG10677, respectively. Thus, of the 23 classic HGPS cases studied, there were only three in which no LMNA mutations were found (Table 2): the two UPD cases (AG10578 and HGADFN005), and the sample with the 6 Mb paternal deletion (C8803).

TABLE 2

| Classical HGPS | Codon 608 seq | Mutation Comment | Mother | Father | Sibling(s) |
|---|---|---|---|---|---|
| AG01972 | GGC/T | G608G | NA | NA | NA |
| AG06297 | GGC/T | G608G | NA | NA | NA |
| AG10801 | A/GGC | *G608S* | NA | NA | NA |
| AG11498 | GGC/T | G608G | NA | NA | NA |
| AG11513 | GGC/T | G608G | NA | NA | NA |
| AG03506 | GGC/T | G608G | Normal | Normal | Normal |
| AG03344 | GGC/T | G608G | Normal | Normal | Normal |
| AG03259 | GGC/T | G608G | Normal | Normal | Normal |
| AG06917 | GGC/T | G608G | Normal | Normal | NA |

TABLE 2 -continued

| Classical HGPS | Codon 608 seq | Mutation | Comment | Mother | Father | Sibling(s) |
|---|---|---|---|---|---|---|
| AG10578 | GGC | | UPD | Normal | NA | Normal |
| AG10579 | GGC/T | G608G | | NA | NA | NA |
| AG10587 | GGC/T | G608G | | Normal | NA | ND |
| HGADFN001 | GGC/T | G608G | | NA | NA | NA |
| HGADFN003 | GGC/T | G608G | | NA | NA | NA |
| HGADFN004 | GGC | | | NA | NA | NA |
| AG10677* | GGC | | | NA | NA | NA |
| HGALBV009 | GGC/T | G608G | | Normal | Normal | NA |
| HGALBV011 | GGC/T | G608G | | Normal | Normal | NA |
| HGALBV057 | GGC/T | G608G | | Normal | Normal | NA |
| HGADFN005 | GGC | | UPD | NA | NA | NA |
| HGADFN008 | GGC/T | G608G | | NA | NA | NA |
| HGADFN014 | GGC/T | G608G | | NA | NA | NA |
| HGALBV071 | GGC/T | G608G | | NA | NA | NA |
| AG10548/C8803 | GGC | | Deletion | Normal | Normal | NA |

NA, not available; seq, nucleotide sequence; *, normal at codon 145.
Additional sequence variants, presumed to be polymorphisms, were identified in exon 3 [L240L (CTG > CTA)], intron 4 (IVS4 + 61C > T), exon 5 [A287A (GCT > GCC)], exon 7 [D446D (GAT > GAC)], intron 8 (IVS8 − 41C > T), and exon 10 [H566H (CAC > CAT)]. The variants in exons 5, 7, and 10 have been previously reported (Genschel & Schmidt, Hum. Mutat. 16:451-459, 2000; Speckman et al., Am. J. Hum. Genet. 66:1192-1198, 2000; Speckman et al., (errata) Am. J. Hum. Genet. 67:775, 2000).

Mechanism of Disease Causation

The most common mutation, G608G(GGC>GGT), is a silent substitution. The second mutation in that same codon, G608S(GGC>AGC), results in a conservative substitution of serine for glycine. How is it possible that these bland-appearing de novo mutations could cause HGPS? Inspection of the normal sequence surrounding codon 608 reveals that both of the observed HGPS mutations improve the match to a consensus splice donor (FIG. 2B), suggesting that they might activate a cryptic splice site.

To confirm this, RT-PCR was performed using a forward primer spanning the junction of exons 7 and 8, and a reverse primer in exon 12. In RNA from unaffected individuals, the expected product appears (FIG. 2C). In RNA samples from cell lines harboring HGPS mutations, an additional smaller RT-PCR product appears. Sequence of these fragments shows that 150 nucleotides within exon 11 are missing. As the reading frame is maintained, this abnormal transcript would be expected to code for a protein with an internal deletion of 50 amino acids near the C-terminus of lamin A. Lamin C would be unaffected.

Cloning and sequencing of the normal full-length fragment obtained from RT-PCR on RNA extracted from primary fibroblasts containing the more common codon 608 mutation revealed that 7/23 clones carry the mutant sequence. Thus, activation of the cryptic splice site within exon 11 is not complete.

In order to determine if the mutant mRNA is actually translated into protein, a Western blot was performed, using a monoclonal antibody against lamin A/C (FIG. 3). In addition to the normal bands for Lamin A and Lamin C, an additional band is present in four of the lanes corresponding to samples from classical HGPS cases, but not in their parents. The abnormal band is not visible in the lane that contains the protein sample from HGPS patient AG11498 [which carries G608G(GGC>GGT)], but this is likely due to the very small amount of lamin A being expressed in this particular fibroblast culture.

Immunofluorescence studies with two different monoclonal antibodies against lamin A/C (FIG. 4) were performed on primary fibroblasts from two unaffected parents (AG06299 and AG06298) and two classical HGPS cases (AG11498 and AG06917), where the common mutation has been identified (Table 2). In 48% of the cells from the samples with classical HGPS, an irregular shape of the nuclear envelope was noted (FIG. 4E-4H). Cells from the unaffected controls (FIG. 4A-4D) showed significantly fewer cells of this phenotype (<6%).

To be certain that this result was not an artifact of secondary differences in the status of the HGPS and control fibroblast cultures, cells originating from the same flasks as the cells used for the immunofluorescence studies were monitored for differences in cell cycle (by fluorescent-activated cell analysis) and degree of apoptosis with propidium iodide and Annexin. No significant differences between the cells derived from the classical HGPS patients and the unaffected parents were noted.

Discussion

Based on the results reported herein, HGPS can now be added to the remarkably long list of human genetic disorders shown to be due to mutations in the LMNA gene. This list includes both dominant and recessive conditions. A review of the available data on genotype-phenotype correlations (Genschel & Schmidt, *Hum. Mutat.* 16:451-459, 2000) suggests that the human phenotype of complete loss of function of LMNA is Emery-Dreifuss muscular dystrophy, and other phenotypes arise from missense changes in various domains of the Lamin A and Lamin C proteins. The HGPS mutation is unusual in two major ways: 1) it involves a large internal deletion of the coding region; 2) it affects lamin A exclusively.

The de novo recurrence of the same exact point mutation in 18 out of 20 cases of classic HGPS is a surprising finding, but is not without precedent. The common HGPS mutation is a C to T in the context of a CpG dinucleotide, which is well known to represent the most mutable base in the vertebrate genome, since a methylated C readily can be deaminated to T and miscopied. A very similar phenomenon occurs in achondroplasia (Shiang et al., *Cell* 78:335-342, 1994; Rousseau et al., *Nature* 371:252-254, 1994), where nearly all sporadic cases are due to CpG to TpG mutations in the FGFR3 gene, resulting in an apparent gain of function mutation (G380R).

Data presented here indicate that the HGPS mutations in codon 608 of LMNA lead to abnormal splicing and a protein product that lacks 50 amino acids near the C-terminus. Extensive prior study of the biochemical function of lamin A suggests a possible mechanism for disease causation. Lamin A is normally synthesized as a precursor molecule (prelamin A). At the C-terminus is a CAAX (SEQ ID NO: 66)-box motif that is subject to farnesylation. Following that, an internal proteolytic cleavage occurs, removing the last 18 coding amino acids (Lutz et al., *Proc. Natl. Acad. Sci. USA* 89:3000-3004, 1992; Sinensky et al., *J. Cell Sci.* 107:61-67, 1994; Hennekes & Nigg, *J. Cell Sci* 107:1019-1029, 1994), to generate mature lamin A. It is predicted that the HGPS mutations and consequent abnormal splicing would produce a prelamin A that still retains the CAAX (SEQ ID NO: 66) box, but is missing the site for endoproteolytic cleavage.

There is also evidence that cell cycle dependent phosphorylation of lamin A is important for its normal function, and at least one site for phosphorylation (Ser625) is deleted in the abnormal HGPS protein (Eggert et al., *Eur. J. Biochem.* 213: 659-671, 1993). As lamin A forms a multiprotein complex within the inner nuclear membrane, this incompletely processed prelamin A may act as a dominant negative. Indeed, the immunofluorescence images (FIG. 4) document major consequences of the HGPS mutations for nuclear membrane stability. Following repeated cell divisions, it can be envisioned that cells expressing the abnormal form of prelamin A may ultimately become nonviable and undergo apoptosis. This might be particularly prominent in cells that are exposed to mechanical shear forces, such as in the cardiovascular and musculoskeletal systems. The delay in appearance of the HGPS phenotype, which generally only becomes apparent at around one year of age, may be due to the developmental timing of expression of lamin A/C, which is generally not expressed in early embryogenesis or in less differentiated cells (Rober et al., *Dev.* 105:365-378, 1989).

Interestingly, defective prelamin A processing recently has been identified in a mouse knockout of the Zmpste24 metalloproteinase (Pendas et al., *Nature Genet.* 31:94-99, 2002; Bergo et al., *Proc. Natl. Acad. Sci. USA* 99:13049-13054, 2002). Zmpste24 is believed to be involved in proteolytic processing of prelamin A, and may represent the actual endoprotease. The homozygote knockout of Zmpste24 presents with a phenotype resembling clinical features observed in HGPS patients, including growth retardation, premature death (20 weeks) from cardiac dysfunction, and alopecia. However, additional features such as pronounced osteoporosis are also present (Bergo et al., *Proc. Natl. Acad. Sci. USA* 99:13049-13054, 2002). Immunofluorescence experiments on cells from these animals show considerable similarity to what is observed in cells from HGPS patients (FIG. 4). A mouse knockout of the LMNA gene has also been previously reported (Sullivan et al., *J. Cell Biol.* 147:913-920, 1999). Severe postnatal growth retardation and muscular dystrophy are observed, and immunofluorescence of nuclei shows elongated and irregular cells with herniation of nuclei.

While the major cause of HGPS appears to be the creation of an abnormal splice donor in exon 11, the finding of a de novo point mutation in exon 2 in a single patient (AG10677) is of interest. In retrospect, this patient (Smith et al., *Am. J. Neuroradiol.* 14:441-443, 1993) had somewhat atypical clinical features (including persistence of coarse hair over the head, ample subcutaneous tissue over the arms and legs, and severe strokes beginning at age 4) that may subtly distinguish this phenotype from classical HGPS.

No LMNA mutations were identified in three of the 23 classical HGPS samples (Table 2). These are the very samples that assisted mapping of the HGPS gene to chromosome 1q. The two UPD cases present an interesting dilemma—if the LMNA gene sequence is normal in both cases, why do they have HGPS? The possibility of imprinting must be considered—but prior cases of both paternal and maternal complete isodisomy of chromosome 1 do not support the presence of any imprinted loci on this chromosome (Pulkkinen et al., *Am. J. Hum. Genet.* 61:611-619, 1997; Gelb et al., *Am. J. Hum. Genet.* 62:848-854, 1998). In the case where DNA samples were available from the mother and sibling (FIG. 1A), we conclude that this phenomenon resulted in a chromosome that has partly paternal and partly maternal alleles. This must have arisen by some kind of post-fertilization event, most likely a mitotic crossover between homologs. Such events may occur rarely in normal development, but would normally not be expected to lead to clonal expansion.

It is currently postulated that these cases actually represent "somatic rescue" events of the premature senescence phenotype of HGPS. Under this hypothesis, the individuals from whom these fibroblasts were derived originally harbored typical codon 608 HGPS mutations in LMNA. Perhaps as an in vivo event, or perhaps as an in vitro event in the fibroblast culture, a mitotic crossover occurred, generating a cell with segmental UPD that had duplicated the wild type allele of LMNA and lost the HGPS mutation. Such a cell would likely then have a growth advantage over its neighbors. This did not happen very early in embryogenesis in the two UPD cases, or they would not have been clinically affected. Proof of this hypothesis would require access to multiple tissues of the deceased UPD patients, which unfortunately are not available.

No mutation in the LMNA gene was identified in the patient with the 6 Mb deletion (FIG. 1C). It is believed that this might also be due to a somatic rescue event—specifically, it is hypothesized that this patient was originally heterozygous for a codon 608 LMNA mutation, but in this instance the "rescue" involved an internal deletion of 6 Mb containing the mutant allele, associated with a more complex mosaic rearrangement of chromosome 1. It is interesting that this patient (and his monozygotic twin) showed particularly severe disease, with contractures present at birth, which might be a consequence of the complete loss of one allele of LMNA in the "rescued" tissues.

Recently, Delgado-Luengo et al. reported on a case of classic HGPS in which an apparent interstitial deletion of chromosome 1q23 was seen (*Am. J. Med. Genet.* 113:298-301, 2002). Cells and DNA were obtained from this patient and surprisingly the typical heterozygous G608G mutation is present. Furthermore, it has not been possible to confirm the presence of an interstitial deletion by high resolution chromosome banding or by FISH with BACs spanning the 1q23-1q24 region. This may be another example of somatic rescue, involving an interstitial deletion in the clone of cells analyzed in the original report, but not present in other samples from the same patient.

The clinical implications of the discovery of the mutational basis of HGPS are twofold. First, since most cases of HGPS appear to have a de novo mutation in the same codon, molecular diagnostics are immediately feasible. This will be particularly useful in making the diagnosis in a young child before the full clinical phenotype has appeared. Molecular diagnostic methods may also provide reassurance in the prenatal arena, where the possibility of parental somatic mosaicism and recurrence of disease in future pregnancies can now be addressed. Second, the delineation of the molecular mechanism provides possible therapeutic approaches. For example, farnesylation inhibitors (such as the statins or farnesyl transferase inhibitors) might reduce the amount of mutant prelamin A. High throughput screens to identify small molecules that reverse the nuclear membrane abnormalities can also now be contemplated.

In addition, the discovery of the molecular basis of HGPS suggests a possible role for LMNA in aspects of the normal aging process. It will be important to look for common variants in this gene that might show association with exceptional longevity, and perhaps also to explore whether somatic mutations in LMNA, accumulated over a lifetime, play some role in senescence.

Example 2

Other LMNA Polymorphisms and/or Mutations

With the provision herein of the correlation between LMNA gene variants and HGPS, the isolation and identification of additional LMNA variants, including variants that lead to progeroid syndromes, is enabled and motivated. Any conventional method for the identification of genetic polymorphisms in a population can be used to identify such additional polymorphisms.

For instance, selective breeding studies in animals are performed to isolate different variants of LMNA. Alternatively, existing populations (e.g., mouse or human populations) are assessed for progeria and/or age-related or premature aging conditions, and individuals within the population (particularly those with symptoms of progeria or other premature aging conditions) are genotyped as relates to an LMNA sequence. These LMNA sequences are then compared to a reference LMNA sequence, such as the normal allele shown herein, to determine the presence of one or more variant nucleotide positions. Once variant nucleotides are identified, statistical analysis of the population is used to determine whether these variants are correlated with progeria and/or another aging-related condition, such as arteriosclerosis and arthrosclerosis.

Alternatively, it is expected that a variant in LMNA that has an effect on normal aging (but is not so severe as to result in a progeroid condition) will be relatively common. In order to study such variants, data can be collected on as many SNPs in LMNA (upstream, downstream, exons, introns) as possible—for instance by surveying public databases, resequencing the gene (e.g., in a number of extremely aged individuals and a number of individuals with average longevity) and analyzing the resultant sequences. How the identified SNPs correlate with their neighbors would be noted, in order to construct "haplotypes." Genotyping of the SNPs that define the haplotypes would then be carried out, to determine whether there are any haplotypes that are overrepresented or underrepresented in individuals of exceptional age.

Also identified are additional mutations in LMNA that are believed to contribute to or be linked to progeroid conditions. These include heterozygous R644c (identified in sample ID AG00989 (atypical progeria); clinical description: diagnosed with atypical progeria and an unspecified type of cachectic dwarfism); heterozygous E145K (identified in sample ID AG10677 (atypical progeria); clinical description: Clinical signs of progeria, including short stature, failure to thrive, partial alopecia of the scalp, dry irregularly hyperpigmented skin, pointed nose, protruding eyes, micrognathia, and high forehead); heterozygous R471C (exon 8) and R527C (exon 9) (identified in sample ID AG07091 (atypical progeria); clinical description: Progeria); and heterozygous A269V (identified in sample ID AG01178 (atypical progeria); clinical description: Progeria).

Example 3

Clinical Uses of LMNA Variants

To perform a diagnostic test for the presence or absence of a polymorphism or mutation in an LMNA sequence of an individual, a suitable genomic DNA-containing sample from a subject is obtained and the DNA extracted using conventional techniques. For instance in some embodiments a blood sample, a buccal swab, a hair follicle preparation, or a nasal aspirate is used as a source of cells to provide the DNA sample. The extracted DNA is then subjected to amplification, for example according to standard procedures. The allele of the single base-pair polymorphism is determined by conventional methods including manual and automated fluorescent DNA sequencing, primer extension methods (Nikiforov, et al., *Nucl Acids Res.* 22:4167-4175, 1994), oligonucleotide ligation assay (OLA) (Nickerson et al., *Proc. Natl. Acad. Sci. USA* 87:8923-8927, 1990), allele-specific PCR methods (Rust et al., *Nucl. Acids Res.* 6:3623-3629, 1993), RNase mismatch cleavage, single strand conformation polymorphism (SSCP), denaturing gradient gel electrophoresis (DGGE), Taq-Man, oligonucleotide hybridization, MALDI-TOF mass spectrometry, and the like. Also, see the following U.S. patent for descriptions of methods or applications of polymorphism analysis to disease prediction and/or diagnosis: U.S. Pat. No. 4,666,828 (RFLP for Huntington's); U.S. Pat. No. 4,801,531 (prediction of atherosclerosis); U.S. Pat. No. 5,110,920 (HLA typing); U.S. Pat. No. 5,268,267 (prediction of small cell carcinoma); and U.S. Pat. No. 5,387,506 (prediction of dysautonomia).

Examples of rare variants associated with progeria, particularly HGPS, and/or an increased likelihood of an age-related condition are the mutations referred to herein as Mutation 1 and Mutation 2. The absence of these or similar mutations in LMNA indicates a relatively low likelihood of carrying or having progeria and a relatively decreased likelihood of having other premature age-related conditions or progeroid conditions (e.g., atypical progeria, cachectic dwarfism). In addition to these particular polymorphisms, other alleles that may be associated with variable predisposition to progeria (e.g., HGPS) can also be detected, and used in combination with the disclosed LMNA polymorphisms to predict the probability that a subject will tend to develop progeria or be likely to develop another age-related condition or disease, or be a genetic carrier of such a likelihood.

For instance, it is believed that mutations in the site for the last step in the post translational processing of prelamin A (i.e., mutations in the RSYLLG motif), may also lead to disease symptoms similar to those seen in progeria subjects, for instance those with a codon 608 mutation as discussed herein. This region is deleted in these mutant alleles, due to the aberrant splicing of exon 11.

The markers of the present disclosure can be utilized for the detection of, and differentiation of, individuals who are heterozygous for the Mutation 1 and/or Mutation 2 variants; it is believed to be extremely unlikely that homozygous individuals would be identified, since the mutations that have been identified are new and occur sporadically. The value of identifying individuals who carry a progeria allele of LMNA (e.g., individuals who are heterozygous for an allele that contains a progeria-linked LMNA polymorphism, such as the G to A base substitution at nucleotide position 1822, or the C to T base substitution at position 1824) is that this allows a precise molecular diagnosis of a condition that is often difficult to be certain of in a young child. Identifying one of these mutations, and showing that it is not present in the parents (as has been the case in every instance so far studied) also allows accurate genetic counseling about a very low recurrence risk, which will be very important for parents who are wondering about future child-bearing. Furthermore, these individuals can then further investigate their health situation regarding premature aging disease.

Example 4

Polymorphism/Mutation Gene Probes and Markers

Sequences surrounding and overlapping single base-pair polymorphisms in the LMNA gene can be useful for a number of gene mapping, targeting, and detection procedures. For example, genetic probes can be readily prepared for hybridization and detection of Mutation 1 or Mutation 2 polymorphisms. As will be appreciated, probe sequences may be greater than about 12 or more oligonucleotides in length and possess sufficient complementarity to distinguish between the alleles. Similarly, sequences surrounding and overlapping either of the specifically disclosed single base-pair polymorphisms (or other polymorphisms found in accordance with the present teachings), or sequences encompassing both specifically disclosed polymorphisms, can be utilized in allele specific hybridization procedures. A similar approach can be adopted to detect other LMNA polymorphisms.

Sequence surrounding and overlapping an LMNA polymorphism, or any portion or subset thereof that allows one to identify the polymorphism, are highly useful. Thus, another embodiment provides a genetic marker predictive of the Mutation 1 polymorphism of LMNA, comprising a partial sequence of the human genome including at least about 10 contiguous nucleotide residues including "N" in the following nucleotide sequence: ggagcccaggtgggnggacccatctc-ctctggct (nucleotides 111-141 of SEQ ID NO: 4), and sequences complementary therewith, wherein "N" represents C or a single base-pair polymorphism of the C that is present at N in a human allele of LMNA. One example polymorphism is a C to T base substitution, but can also include a C to A or C to G base substitution.

Likewise, another specific embodiment is a genetic marker predictive of a Mutation 2 polymorphism of LMNA, comprising a partial sequence of the human genome including at least about 10 contiguous nucleotide residues in the following nucleotide sequence: ggagcccaggtgngcggacccatctcctctggct (nucleotides 111-141 of SEQ ID NO: 5), and sequences complementary therewith, wherein "N" represents G or a single base-pair polymorphism of the G that is present at N in a human allele of LMNA. One example polymorphism is a G to T base substitution, but can also include a G to A or G to C base substitution.

Example 5

Detecting SNPs/Rare Variants

Variants of the normal LMNA sequence, such as those at nucleotide residue 1822 (the first position encoding amino acid residue 608) and/or nucleotide residue 1824 (the last position encoding amino acid 608), can be detected by a variety of techniques. These techniques include allele-specific oligonucleotide hybridization (ASOH) (Stoneking et al., *Am. J. Hum. Genet.* 48:370-382, 1991) which involves hybridization of probes to the sequence, stringent washing, and signal detection. Other new methods include techniques that incorporate more robust scoring of hybridization. Examples of these procedures include the ligation chain reaction (ASOH plus selective ligation and amplification), as disclosed in Wu and Wallace (*Genomics* 4:560-569, 1989); mini-sequencing (ASOH plus a single base extension) as discussed in Syvanen (*Meth. Mol. Biol.* 98:291-298, 1998); and the use of DNA chips (miniaturized ASOH with multiple oligonucleotide arrays) as disclosed in Lipshutz et al. (*Bio Techniques* 19:442-447, 1995). Alternatively, ASOH with single- or dual-labeled probes can be merged with PCR, as in the 5'-exonuclease assay (Heid et al., *Genome Res.* 6:986-994, 1996), or with molecular beacons (as in Tyagi and Kramer, *Nat. Biotechnol.* 14:303-308, 1996).

Another technique is dynamic allele-specific hybridization (DASH), which involves dynamic heating and coincident monitoring of DNA denaturation, as disclosed by Howell et al. (*Nat. Biotech.* 17:87-88, 1999). A target sequence is amplified by PCR in which one primer is biotinylated. The biotinylated product strand is bound to a streptavidin-coated microtiter plate well, and the non-biotinylated strand is rinsed away with alkali wash solution. An oligonucleotide probe, specific for one allele, is hybridized to the target at low temperature. This probe forms a duplex DNA region that interacts with a double strand-specific intercalating dye. When subsequently excited, the dye emits fluorescence proportional to the amount of double-stranded DNA (probe-target duplex) present. The sample is then steadily heated while fluorescence is continually monitored. A rapid fall in fluorescence indicates the denaturing temperature of the probe-target duplex. Using this technique, a single-base mismatch between the probe and target results in a significant lowering of melting temperature ($T_m$) that can be readily detected.

A variety of other techniques can be used to detect the variations in DNA. Merely by way of example, a variety of detection techniques can be found in U.S. Pat. Nos. 4,666,828; 4,801,531; 5,110,920; 5,268,267; 5,387,506; 5,691,153; 5,698,339; 5,736,330; 5,834,200; 5,922,542; and 5,998,137 for such methods. In specifically contemplated embodiments, variations in sequence are detected using MALDI-TOF mass spectrophotometery.

Example 6

Detection of LMNA Nucleic Acid Level(s)

Individuals carrying mutations in the LMNA gene, or having amplifications or heterozygous deletions of the LMNA gene, may be detected at the DNA or RNA level with the use of a variety of techniques. The detection of point mutations was discussed above; in the following example, techniques are provided for detecting the level of LMNA nucleic acid molecules in a sample.

For such diagnostic procedures, a biological sample of the subject (an animal, such as a mouse or a human), which biological sample contains either DNA or RNA derived from the subject, is assayed for a mutated, amplified or deleted LMNA encoding sequence, such as a genomic amplification of the LMNA gene or an over- or under-abundance of a LMNA mRNA. Suitable biological samples include samples containing genomic DNA or mRNA obtained from subject body cells, such as those present in peripheral blood, urine, saliva, tissue biopsy, surgical specimen, amniocentesis samples and autopsy material. The detection in the biological sample of a mutant LMNA gene, a mutant LMNA RNA, or an amplified or homozygously or heterozygously deleted LMNA gene, may be performed by a number of methodologies.

Gene dosage (copy number) can be important in disease states, and can influence mRNA and thereby protein level; it is therefore advantageous to determine the number of copies of LMNA nucleic acids in samples of tissue. Probes generated from the encoding sequence of LMNA (LMNA probes or primers) can be used to investigate and measure genomic dosage of the LMNA gene.

Appropriate techniques for measuring gene dosage are known in the art; see for instance, U.S. Pat. No. 5,569,753 ("Cancer Detection Probes") and Pinkel et al. (*Nat. Genet.* 20:207-211, 1998) ("High Resolution Analysis of DNA Copy Number Variation using Comparative Genomic Hybridization to Microarrays").

Determination of gene copy number in cells of a patient-derived sample using other techniques is known in the art. By way of example, interphase FISH analysis of immortalized cell lines can be carried out as previously described (Barlund et al., *Genes Chromo. Cancer* 20:372-376, 1997). The hybridizations can be evaluated using a Zeiss fluorescence microscope. By way of example, approximately 20 non-overlapping nuclei with intact morphology based on DAPI counterstain are scored to determine the mean number of hybridization signals for each test and reference probe.

Likewise, FISH can be performed on tissue microarrays, as described in Kononen et al., *Nat. Med.* 4:844-847, 1998. Briefly, consecutive sections of the array are deparaffinized, dehydrated in ethanol, denatured at 74° C. for 5 minutes in 70% formamide/2×SSC, and hybridized with test and reference probes. The specimens containing tight clusters of signals or >3-fold increase in the number of test probe as compared to chromosome 17 centromere in at least 10% of the tumor cells may be considered as amplified. Microarrays using various tissues can be constructed as described in WO9944063 and WO9944062.

Overexpression or under expression of the LMNA gene can also be detected by measuring the cellular level of LMNA-specific mRNA. mRNA can be measured using techniques well known in the art, including for instance Northern analysis, RT-PCR and mRNA in situ hybridization. Additionally, since splice variants such as the one identified herein as Mutation 1 produce different length mRNAs compared to those produced from normal (wildtype) LMNA, changes can be detected by examining transcripts on a Northern blot.

Example 7

Expression of Lamin A Polypeptides

The expression and purification of proteins, such as the Lamin A protein, can be performed using standard laboratory techniques. After expression, purified Lamin A protein may be used for functional analyses, antibody production, diagnostics, and patient therapy. Furthermore, the DNA sequence of the LMNA/Lamin A cDNA can be manipulated in studies to understand the expression of the gene and the function of its product. Mutant forms of the human LMNA gene may be isolated based upon information contained herein, and may be studied in order to detect alteration in expression patterns in terms of relative quantities, tissue specificity and functional properties of the encoded mutant Lamin A protein. Partial or full-length cDNA sequences, which encode for the subject protein, may be ligated into bacterial expression vectors. Methods for expressing large amounts of protein from a cloned gene introduced into *Escherichia coli* (*E. coli*) may be utilized for the purification, localization and functional analysis of proteins. For example, fusion proteins consisting of amino terminal peptides encoded by a portion of the *E. coli* lacZ or trpE gene linked to Lamin A proteins may be used to prepare polyclonal and monoclonal antibodies against these proteins. Thereafter, these antibodies may be used to purify proteins by immunoaffinity chromatography, in diagnostic assays to quantitate the levels of protein and to localize proteins in tissues and individual cells by immunofluorescence.

Intact native protein may also be produced in *E. coli* in large amounts for functional studies. Methods and plasmid vectors for producing fusion proteins and intact native proteins in bacteria are described in Sambrook et al. (In *Molecular Cloning: A Laboratory Manual*, Ch. 17, CSHL, New York, 1989). Such fusion proteins may be made in large amounts, are easy to purify, and can be used to elicit antibody response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX1-3 (Stanley and Luzio, EMBO J. 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986). Lamin A fusion proteins may be isolated from protein gels, lyophilized, ground into a powder and used as an antigen. The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous LMNA cDNA.

For expression in mammalian cells, the cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR.

The cDNA sequence (or portions derived from it) or a mini gene (a cDNA with an intron and its own promoter) may be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78: 2072-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985)) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis. One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is now a conventional technique. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell. Biol.* 7:2013, 1987), electroporation (Neumann et al., *EMBO J.* 1:841, 1982), lipofection (Felgner et al., *Proc. Natl. Acad. Sci. USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Lamin A-encoding sequences, including sequences encoding mutant forms of Lamin A, can also be delivered to target cells in vitro via non-infectious systems, for instance liposomes.

These eukaryotic expression systems can be used for studies of Lamin A encoding nucleic acids and mutant forms of these molecules, the Lamin A protein and mutant forms of this protein. Such uses include, for example, the identification of regulatory elements located in the 5' region of the LMNA gene on genomic clones that can be isolated from human genomic DNA libraries using the information contained in the present disclosure. The eukaryotic expression systems may also be used to study the function of the normal complete protein, specific portions of the protein, or of naturally occurring or artificially produced mutant proteins.

Using the above techniques, the expression vectors containing the LMNA gene sequence or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, *Cell* 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts or lymphoblasts may be used.

The present disclosure thus encompasses recombinant vectors that comprise all or part of the LMNA gene or cDNA sequences, for expression in a suitable host. The LMNA DNA is operatively linked in the vector to an expression control sequence in the recombinant DNA molecule so that the Lamin A polypeptide can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the trp system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

The host cell, which may be transfected with the vector of this disclosure, may be selected from the group consisting of *E. coli, Pseudomonas, Bacillus subtilis, Bacillus stearothermophilus* or other bacilli; other bacteria; yeast; fungi; insect; mouse or other animal; or plant hosts; or human tissue cells.

It is appreciated that for mutant or variant LMNA DNA sequences, similar systems are employed to express and produce the mutant product. In addition, fragments of the Lamin A protein can be expressed essentially as detailed above. Such fragments include individual Lamin A protein domains or sub-domains, as well as shorter fragments such as peptides. Lamin A protein fragments having therapeutic properties may be expressed in this manner also.

Further, specifically contemplated are constructs that include a Lamin A protein, particularly a variant such as the provided mutant form, functionally linked to a tag. Examples of tags include generally epitope tags, purification tags, and identification tags. Specific examples of peptide tags include a FLAG tag, a c-myc tag, a 6×His tag, a HA tag, a T7 tag, a GFP peptide, and a GST peptide.

Example 8

Production of Lamin A Protein Specific Binding Agents

Monoclonal or polyclonal antibodies may be produced to either the normal Lamin A protein or mutant forms of this protein. Optimally, antibodies raised against these proteins or peptides would specifically detect the protein or peptide with which the antibodies are generated, or in some instances, a particular mutation form of that protein. That is, an antibody generated to the Lamin A protein or a fragment thereof would recognize and bind the Lamin A protein and would not substantially recognize or bind to other proteins found in human cells.

The determination that an antibody specifically detects the Lamin A protein is made by any one of a number of standard immunoassay methods; for instance, the Western blotting technique (Sambrook et al., In *Molecular Cloning: A Laboratory Manual*, CSHL, New York, 1989). To determine that a given antibody preparation (such as one produced in a mouse) specifically detects the Lamin A protein by Western blotting, total cellular protein is extracted from human cells (for example, lymphocytes) and electrophoresed on a sodium dodecyl sulfate-polyacrylamide gel. The proteins are then transferred to a membrane (for example, nitrocellulose) by Western blotting, and the antibody preparation is incubated with the membrane. After washing the membrane to remove non-specifically bound antibodies, the presence of specifically bound antibodies is detected by the use of an anti-mouse antibody conjugated to an enzyme such as alkaline phosphatase. Application of an alkaline phosphatase substrate 5-bromo-4-chloro-3-indolyl phosphate/nitro blue tetrazolium results in the production of a dense blue compound by immunolocalized alkaline phosphatase. Antibodies that specifically detect the Lamin A protein will, by this technique, be shown to bind to the Lamin A protein band (which will be localized at a given position on the gel determined by its molecular weight). Non-specific binding of the antibody to other proteins may occur and may be detectable as a weak signal on the Western blot. The non-specific nature of this binding will be recognized by one skilled in the art by the weak signal obtained on the Western blot relative to the strong primary signal arising from the specific antibody-Lamin A protein binding.

Substantially pure Lamin A protein or protein fragment (peptide) suitable for use as an immunogen may be isolated from the transfected or transformed cells as described above. Concentration of protein or peptide in the final preparation is adjusted, for example, by concentration on an Amicon filter device, to the level of a few micrograms per milliliter. Monoclonal or polyclonal antibody to the protein can then be prepared as follows:

A. Monoclonal Antibody Production by Hybridoma Fusion

Monoclonal antibody to epitopes of the Lamin A protein can be prepared from murine hybridomas according to the classical method of Kohler and Milstein (*Nature* 256:495-497, 1975) or derivative methods thereof. Briefly, a mouse is repetitively inoculated with a few micrograms of the selected protein over a period of a few weeks. The mouse is then sacrificed, and the antibody-producing cells of the spleen isolated. The spleen cells are fused by means of polyethylene glycol with mouse myeloma cells, and the excess un-fused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall (*Meth. Enzymol.* 70:419-439, 1980), and derivative methods thereof. Selected positive clones can be expanded and their monoclonal antibody product harvested for use. Detailed procedures for monoclonal antibody production are described in Harlow and Lane (*Antibodies, A Laboratory Manual*, CSHL, New York, 1988).

B. Polyclonal Antibody Production by Immunization

Polyclonal antiserum containing antibodies to heterogeneous epitopes of a single protein can be prepared by immunizing suitable animals with the expressed protein, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with either inadequate or excessive doses of antigen resulting in low titer antisera. Small doses (ng level) of antigen administered at multiple intradermal sites appear to be most reliable. An effective immunization protocol for rabbits can be found in Vaitukaitis et al. (*J. Clin. Endocrinol. Metab.* 33:988-991, 1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony et al. (In *Handbook of Experimental Immunology*, Wier, D. (ed.) chapter 19. Blackwell, 1973). Plateau concentration of antibody is usually in the range of about 0.1 to 0.2 mg/ml of serum (about 12 µM). Affinity of the antisera for the antigen is determined by preparing competitive binding curves, as described, for example, by Fisher (*Manual of Clinical Immunology*, Ch. 42, 1980).

C. Antibodies Raised Against Synthetic Peptides

A third approach to raising antibodies against a Lamin A protein or peptides is to use one or more synthetic peptides synthesized on a commercially available peptide synthesizer based upon the predicted amino acid sequence of a Lamin A protein or peptide. Polyclonal antibodies can be generated by injecting these peptides into, for instance, rabbits.

It is particularly contemplated that antibodies can be raised that are specific for the variant/mutant protein provided herein. For instance, such variant-specific antibodies can be generated by using an epitope that represents the abnormal junction between the middle of exon 11 and exon 12, as described herein. An immunogen of SGSGAQSPQNC (positions 601 to 611 of SEQ ID NO: 7) would be an example. An antibody that recognizes this epitope, but not wild type lamin A, can be used for a very specific diagnostic test for HGPS. Even more than that, this antibody might be useful as a therapeutic, since it would target the mutant protein and not the normal one.

D. Antibodies Raised by Injection of Lamin A Encoding Sequence

Antibodies may be raised against Lamin A proteins and peptides by subcutaneous injection of a DNA vector that expresses the desired protein or peptide, or a fragment thereof, into laboratory animals, such as mice. Delivery of the recombinant vector into the animals may be achieved using a hand-held form of the Biolistic system (Sanford et al., *Particulate Sci. Technol.* 5:27-37, 1987) as described by Tang et al. (*Nature* 356:152-154, 1992). Expression vectors suitable for this purpose may include those that express the Lamin A encoding sequence under the transcriptional control of either the human β-actin promoter or the cytomegalovirus (CMV) promoter.

Antibody preparations, such as those prepared according to any of these protocols, are useful in quantitative immunoassays that determine concentrations of antigen-bearing substances in biological samples; they are also used semi-quantitatively or qualitatively to identify the presence of antigen in a biological sample; or for immunolocalization of the Lamin A protein.

For administration to human patients, antibodies, e.g., Lamin A specific monoclonal antibodies, can be humanized by methods known in the art. Antibodies with a desired binding specificity can be commercially humanized (Scotgene, Scotland, UK; Oxford Molecular, Palo Alto, Calif.).

In addition, antibodies to Lamin A are commercially available. See, for instance, Covance Research Products (CRP, Inc., Denver, Pa., USA) Catalog Number MMS-107R, a monoclonal antibody that recognizes both Lamin A and Lamin C.

Example 9

Protein-Based Diagnosis and Detection

An alternative method of detecting abnormalities in LMNA, including for instance gene amplification, deletion or mutation, as well as abnormal Lamin A expression, is to quantitate the level of Lamin A protein and/or determine its molecular weight in the cells of an individual. This diagnostic tool would be useful for detecting reduced levels of the Lamin A protein that result from, for example, mutations in the promoter regions of the LMNA gene or mutations within the coding region of the gene that produced truncated, non-functional or unstable polypeptides, as well as from deletions of a portion of or the entire LMNA gene. Alternatively, duplications of a Lamin A encoding sequence may be detected as an increase in the expression level of Lamin A protein. Such an increase in protein expression may also be a result of an up-regulating mutation in the promoter region or other regulatory or coding sequence within the LMNA gene. Localization and/or coordinated Lamin A expression (temporally or spatially) can also be examined using known techniques, such as isolation and comparison Lamin A from cell or tissue specific, or time specific, samples.

The determination of reduced or increased Lamin A protein levels, in comparison to such expression in a control cell (e.g., normal, as in taken from a subject not suffering from progeria, such as HGPS), would be an alternative or supplemental approach to the direct determination of LMNA gene deletion, amplification or mutation status by the methods outlined above and equivalents.

The availability of antibodies specific to the Lamin A protein will facilitate the detection and quantitation of cellular Lamin A by one of a number of immunoassay methods which are well known in the art and are presented in Harlow and Lane (*Antibodies, A Laboratory Manual*, CSHL, New York, 1988). Methods of constructing such antibodies are discussed above, and Lamin-specific antibodies are available commercially.

Any standard immunoassay format (e.g., ELISA, Western blot, or RIA assay) can be used to measure Lamin A polypeptide or protein levels; comparison is to wild-type (normal) Lamin A levels, and an alteration in Lamin A polypeptide may be indicative of an abnormal biological condition such as progeria and/or a predilection to development of a premature aging disease or condition. Immunohistochemical techniques may also be utilized for Lamin A polypeptide or protein detection. For example, a tissue sample may be obtained from a subject, and a section stained for the presence of Lamin A using a Lamin A specific binding agent (e.g., anti-Lamin A antibody) and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (*Current Protocols in Molecular Biology*, John Wiley & Sons, New York, 1998).

For the purposes of quantitating a Lamin A protein, a biological sample of the subject (which can be any animal, for instance a mouse or a human), which sample includes cellular proteins, is required. Such a biological sample may be obtained from body cells, such as those present in peripheral blood, urine, saliva, tissue biopsy, amniocentesis samples, surgical specimens and autopsy material, particularly breast cells. Quantitation of Lamin A protein can be achieved by immunoassay and compared to levels of the protein found in control cells (e.g., healthy, as in from a patient known not to have progeria). A significant (e.g., 10% or greater) reduction in the amount of Lamin A protein in the cells of a subject compared to the amount of Lamin A protein found in normal human cells could be taken as an indication that the subject may have deletions or mutations in the LMNA gene, whereas a significant (e.g., 10% or greater) increase would indicate that a duplication (amplification), or mutation that increases the stability of the Lamin A protein or mRNA, may have occurred. Deletion, mutation and/or amplification of or within the Lamin A encoding sequence, and substantial under- or over-expression of Lamin A protein, may be indicative of progeria and/or a predilection to develop or carry an allele for a premature aging disease or condition.

Since it is predicted that Mutations 1 and 2 will produce a protein that is 50 amino acids shorter than the wild type Lamin A, a convenient diagnostic method to identify HGPS is to perform a Western blot and look for the abnormal (shorter) band.

Example 10

Differentiation of Individuals Homozygous versus Heterozygous for the Variant(s)

As will be appreciated by those of ordinary skill in the art, the oligonucleotide ligation assay (OLA), as described at Nickerson et al. (*Proc. Natl. Acad. Sci. USA* 87:8923-8927, 1990), allows the differentiation between individuals who are homozygous versus heterozygous for variant sequences in the LMNA gene, for instance either the Mutation 1 or the Mutation 2 variants. This allows one to rapidly and easily determine whether an individual is homozygous for at least one progeria-linked variant or other polymorphism, which condition is linked to a relatively high predisposition to developing progeria and/or an increased likelihood of an age-related disease or condition, such as arthrosclerosis. Alternatively, OLA can be used to determine whether a subject is homozygous for a polymorphism identified in the LMNA gene.

As an example of the OLA assay, when carried out in microtiter plates, one well is used for the determination of the presence of the LMNA allele that contains a G at nucleotide position 1822 and a second well is used for the determination of the presence of the LMNA allele that contains an A at nucleotide position 1822. Thus, the results for an individual who is heterozygous for the polymorphism will show a signal in each of the G and A wells, and an individual who is homozygous for the Mutation 2 polymorphism will show a signal in only the A well.

Example 11

Suppression of Lamin A Expression

A reduction of Lamin A protein expression in a cell may be obtained by introducing into cells an antisense construct based on the LMNA encoding sequence, including the human LMNA cDNA or gene sequence (as shown herein) or flanking regions thereof. For antisense suppression, a nucleotide sequence from a Lamin A encoding sequence, e.g. all or a portion of the LMNA cDNA or gene, is arranged in reverse orientation relative to the promoter sequence in the transformation vector. Other aspects of the vector may be chosen as discussed herein and are well known.

The introduced sequence need not be the full length human LMNA cDNA or gene or reverse complement thereof, and need not be exactly homologous to the equivalent sequence found in the cell type to be transformed. Generally, however, where the introduced sequence is of shorter length, a higher degree of homology to the native LMNA sequence will be needed for effective antisense suppression. The introduced antisense sequence in the vector may be at least 30 nucleotides in length, and improved antisense suppression will typically be observed as the length of the antisense sequence increases. The length of the antisense sequence in the vector advantageously may be greater than 100 nucleotides. For suppression of the LMNA gene itself, transcription of an antisense construct results in the production of RNA molecules that are the reverse complement of mRNA molecules transcribed from the endogenous LMNA gene in the cell.

Although the exact mechanism by which antisense RNA molecules interfere with gene expression has not been elucidated, it is believed that antisense RNA molecules bind to the endogenous mRNA molecules and thereby inhibit translation of the endogenous mRNA.

Expression of Lamin A can also be reduced using small inhibitory RNAs, for instance using techniques similar to those described previously (see, e.g., Tuschl et al., *Genes Dev* 13, 3191-3197, 1999; Caplen et al., *Proc. Nat'l Acad. Sci. USA* 98, 9742-9747, 2001; and Elbashir et al., *Nature* 411, 494-498, 2001). In particular, methods are contemplated using an RNAi that is targeted at the abnormal splice junction in mutant Lamin A, which could shut off the abnormal protein and not the normal one.

Suppression of endogenous Lamin A expression can also be achieved using ribozymes. Ribozymes are synthetic RNA molecules that possess highly specific endoribonuclease activity. The production and use of ribozymes are disclosed in U.S. Pat. No. 4,987,071 to Cech and U.S. Pat. No. 5,543,508 to Haselhoff. The inclusion of ribozyme sequences within antisense RNAs may be used to confer RNA cleaving activity on the antisense RNA, such that endogenous mRNA molecules that bind to the antisense RNA are cleaved, which in turn leads to an enhanced antisense inhibition of endogenous gene expression.

Finally, dominant negative mutant forms of Lamin A may be used to block endogenous Lamin A activity. For instance, it is believed that mutant 1 and mutant 2 as described herein are dominant negative mutations.

Example 12

LMNA Gene Therapy

Gene therapy approaches for combating or treating progeria, or reducing the risk of premature aging disease or conditions, in subjects are now made possible by the present disclosure.

Retroviruses have been considered a preferred vector for experiments in gene therapy, with a high efficiency of infection and stable integration and expression (Orkin et al., *Prog. Med. Genet.* 7:130-142, 1988). The full-length LMNA gene or cDNA can be cloned into a retroviral vector and driven from either its endogenous promoter or from the retroviral LTR (long terminal repeat). Other viral transfection systems may also be utilized for this type of approach, including adenovirus, adeno-associated virus (AAV) (McLaughlin et al., *J. Virol.* 62:1963-1973, 1988), Vaccinia virus (Moss et al., *Annu. Rev. Immunol.* 5:305-324, 1987), Bovine Papilloma virus (Rasmussen et al., *Methods Enzymol.* 139:642-654, 1987) or members of the herpesvirus group such as Epstein-Barr virus (Margolskee et al., *Mol. Cell. Biol.* 8:2837-2847, 1988).

Gene therapy techniques include the use of RNA-DNA hybrid oligonucleotides, as described by Cole-Strauss, et al. (*Science* 273:1386-1389, 1996). This technique may allow for site-specific integration of cloned sequences, thereby permitting accurately targeted gene replacement.

In addition to delivery of a Lamin A encoding sequence to cells using viral vectors, it is possible to use non-infectious methods of delivery. For instance, lipidic and liposome-mediated gene delivery has recently been used successfully for transfection with various genes (for reviews, see Templeton and Lasic, *Mol. Biotechnol.* 11:175-180, 1999; Lee and Huang, *Crit. Rev. Ther. Drug Carrier Syst.* 14:173-206; and Cooper, *Semin. Oncol.* 23:172-187, 1996). For instance, cationic liposomes have been analyzed for their ability to transfect monocytic leukemia cells, and shown to be a viable alternative to using viral vectors (de Lima et al., *Mol. Membr. Biol.* 16:103-109, 1999). Such cationic liposomes can also be targeted to specific cells through the inclusion of, for instance, monoclonal antibodies or other appropriate targeting ligands (Kao et al., *Cancer Gene Ther.* 3:250-256, 1996).

To reduce the level of Lamin A expression, gene therapy can be carried out using antisense or other suppressive constructs, the construction of which is discussed above.

Example 13

Kits

Kits are provided which contain the necessary reagents for determining the presence or absence of polymorphism(s) in a Lamin A-encoding sequence, such as probes or primers specific for the LMNA gene. Such kits can be used with the methods described herein to determine whether a subject is predisposed to or heterozygous for progeria, or otherwise likely to suffer from a premature aging disease or condition.

The provided kits may also include written instructions. The instructions can provide calibration curves or charts to compare with the determined (e.g., experimentally measured) values. Kits are also provided to determine elevated or depressed expression of mRNA (e.g., containing probes) or Lamin A protein (e.g., containing antibodies or other Lamin A-protein specific binding agents).

A. Kits for Amplification of LMNA Sequences

The oligonucleotide probes and primers that can hybridize to a LMNA sequence, and particularly a sequence in or near exon 11 of LMNA, can be supplied in the form of a kit for use in detection of, for instance, a predisposition to progeria in a subject. In such a kit, an appropriate amount of one or more of the oligonucleotide primers is provided in one or more containers. The oligonucleotide primers may be provided suspended in an aqueous solution or as a freeze-dried or lyophilized powder, for instance. The container(s) in which the oligonucleotide(s) are supplied can be any conventional container that is capable of holding the supplied form, for instance, microfuge tubes, ampoules, or bottles. In some applications, pairs of primers may be provided in pre-measured single use amounts in individual, typically disposable, tubes or equivalent containers. With such an arrangement, the sample to be tested for the presence of an LMNA polymorphism can be added to the individual tubes and amplification carried out directly.

The amount of each oligonucleotide primer supplied in the kit can be any appropriate amount, depending for instance on the market to which the product is directed. For instance, if the kit is adapted for research or clinical use, the amount of each oligonucleotide primer provided would likely be an amount sufficient to prime several PCR amplification reactions. Those of ordinary skill in the art know the amount of oligonucleotide primer that is appropriate for use in a single amplification reaction. General guidelines may for instance be found in Innis et al. (*PCR Protocols, A Guide to Methods and Applications*, Academic Press, Inc., San Diego, Calif., 1990), Sambrook et al. (In *Molecular Cloning: A Laboratory Manual*, Cold Spring Harbor, N.Y., 1989), and Ausubel et al. (In *Current Protocols in Molecular Biology*, Greene Publ. Assoc. and Wiley-Intersciences, 1992).

A kit may include more than two primers, in order to facilitate the in vitro amplification of LMNA sequences, for instance the LMNA gene or the 5' or 3' flanking region thereof.

In some embodiments, kits may also include the reagents necessary to carry out nucleotide amplification reactions, including, for instance, DNA sample preparation reagents, appropriate buffers (e.g., polymerase buffer), salts (e.g., magnesium chloride), and deoxyribonucleotides (dNTPs).

Kits may in addition include either labeled or unlabeled oligonucleotide probes for use in detection of LMNA polymorphism(s). In certain embodiments, these probes will be specific for a potential polymorphism that may be present in the target amplified sequences. The appropriate sequences for such a probe will be any sequence that includes one or more of the identified polymorphic sites, particularly nucleotide positions 1822 and 1824, such that the sequence of the probe is complementary to a polymorphic site and the surrounding LMNA sequence.

It may also be advantageous to provide in the kit one or more control sequences for use in the amplification reactions. The design of appropriate positive control sequences is well known to one of ordinary skill in the appropriate art.

B. Kits for Detection of LMNA mRNA Expression

Kits similar to those disclosed above for the detection of LMNA polymorphisms directly can be used to detect LMNA mRNA expression, such as over- or under-expression. Such kits include an appropriate amount of one or more oligonucleotide primers for use in, for instance, reverse transcription PCR reactions, similarly to those provided above with art-obvious modifications for use with RNA amplification.

In some embodiments, kits for detection of altered expression of LMNA mRNA may also include some or all of the reagents necessary to carry out RT-PCR in vitro amplification reactions, including, for instance, RNA sample preparation reagents (including e.g., an RNase inhibitor), appropriate buffers (e.g., polymerase buffer), salts (e.g., magnesium chloride), and deoxyribonucleotides (dNTPs). Written instructions may also be included.

Such kits may in addition include either labeled or unlabeled oligonucleotide probes for use in detection of the in vitro amplified target sequences. The appropriate sequences for such a probe will be any sequence that falls between the annealing sites of the two provided oligonucleotide primers, such that the sequence the probe is complementary to is amplified during the PCR reaction. In certain embodiments, these probes will be specific for a potential polymorphism that may be present in the target amplified sequences, for instance specific for the Mutation 1 allele (e.g., capable of detecting a T residue at position 1824 of the LMNA sequence).

It may also be advantageous to provide in the kit one or more control sequences for use in the RT-PCR reactions. The design of appropriate positive control sequences is well known to one of ordinary skill in the appropriate art.

Alternatively, kits may be provided with the necessary reagents to carry out quantitative or semi-quantitative Northern analysis of LMNA mRNA. Such kits include, for instance, at least one LMNA-specific oligonucleotide for use as a probe. This oligonucleotide may be labeled in any conventional way, including with a selected radioactive isotope, enzyme substrate, co-factor, ligand, chemiluminescent or fluorescent agent, hapten, or enzyme. In certain embodiments, such probes will be specific for a potential polymorphism that may be present in the target amplified sequences, for instance specific for the Mutation 1 allele (e.g., capable of detecting a T residue at position 1824 of the LMNA sequence).

C. Kits for Detection of Lamin A Protein Expression

Kits for the detection of Lamin A protein expression (such as over- or under-expression, or expression of a protein of a different length than found in a normal cell) are also encompassed. Such kits may include at least one target protein specific binding agent (e.g., a polyclonal or monoclonal antibody or antibody fragment that specifically recognizes the Lamin A protein) and may include at least one control (such as a determined amount of Lamin A protein, or a sample containing a determined amount of Lamin A protein). The Lamin A-protein specific binding agent and control may be contained in separate containers.

The Lamin A protein expression detection kits may also include a means for detecting Lamin A:binding agent complexes, for instance the agent may be detectably labeled. If the detectable agent is not labeled, it may be detected by second antibodies or protein A for example which may also be provided in some kits in one or more separate containers. Such techniques are well known.

Additional components in specific kits may include instructions for carrying out the assay. Instructions will allow the tester to determine whether Lamin A expression levels are elevated. Reaction vessels and auxiliary reagents such as chromogens, buffers, enzymes, etc. may also be included in the kits.

D. Kits for Detection of Homozygous versus Heterozygous Allelism

Also provided are kits that allow differentiation between individuals who are homozygous versus heterozygous for either the Mutation 1 or the Mutation 2 polymorphisms of LMNA. Such kits provide the materials necessary to perform oligonucleotide ligation assays (OLA), as described at Nickerson et al. (*Proc. Natl. Acad. Sci. USA* 87:8923-8927, 1990). In specific embodiments, these kits contain one or more microtiter plate assays, designed to detect polymorphism(s) in the LMNA sequence of a subject, as described herein.

Additional components in some of these kits may include instructions for carrying out the assay. Instructions will allow the tester to determine whether a LMNA allele is homozygous or heterozygous. Reaction vessels and auxiliary reagents such as chromogens, buffers, enzymes, etc. may also be included in the kits.

It may also be advantageous to provide in the kit one or more control sequences for use in the OLA reactions. The design of appropriate positive control sequences is well known to one of ordinary skill in the appropriate art.

Example 14

Lamin A Knockout and Overexpression Transgenic Animals

Mutant organisms that under-express or over-express Lamin A protein are useful for research. Such mutants allow insight into the physiological and/or pathological role of Lamin A in a healthy and/or pathological organism, for instance in characterization of aging and aging-related diseases and conditions, including progeria. These mutants are "genetically engineered," meaning that information in the form of nucleotides has been transferred into the mutant's genome at a location, or in a combination, in which it would not normally exist. Nucleotides transferred in this way are said to be "non-native." For example, a non-LMNA promoter inserted upstream of a native LMNA encoding sequence would be non-native. An extra copy of an LMNA gene on a plasmid, transformed into a cell, would be non-native.

Mutants may be, for example, produced from mammals, such as mice, that either over-express Lamin A or under-express Lamin A, or that do not express Lamin A at all, or that express a mutant form of Lamin A (such as the splice variant produced by the Mutation 1 allele described herein). Over-expression mutants are made by increasing the number of LMNA genes in the organism, or by introducing an LMNA gene into the organism under the control of a constitutive or inducible or viral promoter such as the mouse mammary tumor virus (MMTV) promoter or the whey acidic protein (WAP) promoter or the metallothionein promoter. Mutants that under-express Lamin A may be made by using an inducible or repressible promoter, or by deleting the LMNA gene, or by destroying or limiting the function of the LMNA gene, for instance by disrupting the gene by transposon insertion.

Antisense "genes" or siRNA constructs may be engineered into the organism, under a constitutive or inducible promoter, to decrease or prevent Lamin A expression, as discussed above.

A gene is "functionally deleted" when genetic engineering has been used to negate or reduce gene expression to negligible levels. When a mutant is referred to in this application as having the LMNA gene altered or functionally deleted, this refers to the LMNA gene and to any ortholog of this gene. When a mutant is referred to as having "more than the normal copy number" of a gene, this means that it has more than the usual number of genes found in the wild-type organism, e.g., in the diploid mouse or human.

A mutant mouse over-expressing normal or mutant Lamin A may be made by constructing a plasmid having an LMNA encoding sequence driven by a promoter, such as the mouse mammary tumor virus (MMTV) promoter or the whey acidic protein (WAP) promoter. This plasmid may be introduced into mouse oocytes by microinjection. The oocytes are implanted into pseudopregnant females, and the litters are assayed for insertion of the transgene. Multiple strains containing the transgene are then available for study.

WAP is quite specific for mammary gland expression during lactation, and MMTV is expressed in a variety of tissues including mammary gland, salivary gland and lymphoid tissues. Many other promoters might be used to achieve various patterns of expression, e.g., the metallothionein promoter.

An inducible system may be created in which the subject expression construct is driven by a promoter regulated by an agent that can be fed to the mouse, such as tetracycline. Such techniques are well known in the art.

In particular, one example transgenic animal is a mouse model of HGPS, duplicating one of the G608G mutations. The mouse sequence is perfectly identical here, so this would produce the same kind of consequence for lamin A as in the human.

Example 15

Knock-In Organisms

In addition to knock-out systems, it is also beneficial to generate "knock-ins" that have lost expression of the wild-type protein but have gained expression of a different, usually mutant form of the same protein.

By way of example, the dominant mutant Lamin A protein provided herein can be expressed in a knockout background, such as a mutant mouse that has been rendered defective or selectively defective (e.g., inducibly knocked-out) for LMNA expression, in order to provide model systems for studying the effects of the dominant mutant protein. In particular embodiments, the resultant knock-in organisms provide systems for studying aging, arteriosclerosis, and/or HGPS-like conditions.

Those of ordinary skill in the relevant art know methods of producing knock-in organisms. See, for instance, Rane et al. (*Mol. Cell Biol.,* 22: 644-656, 2002); Sotillo et al. (*EMBO J.,* 20: 6637-6647, 2001); Luo et al. (*Oncogene,* 20: 320-328, 2001); Tomasson et al. (*Blood,* 93: 1707-1714, 1999); Voncken et al. (*Blood,* 86: 4603-4611, 1995); Andrae et al. (*Mech. Dev.,* 107: 181-185, 2001); Reinertsen et al. (*Gene Expr.,* 6: 301-314, 1997); Huang et al. (*Mol. Med.,* 5: 129-137, 1999) by way of example.

Example 16

Development of Therapeutic Compounds

This disclosure further relates in some embodiments to novel methods for screening test compounds for their ability to treat, detect, analyze, ameliorate, reverse, and/or prevent diseases or conditions mediated by mutations in LMNA, and particularly dominant mutations such as Mutation 1 and Mutation 2, which generate truncation mutant forms of Lamin A, and other mutations in LMNA. In particular, the present disclosure provides methods for identifying test compounds that can be used to treat, ameliorate, reverse, and/or prevent aging-related or associated diseases or conditions, including HGPS and other progeroid conditions and diseases, arteriosclerosis and athrosclerosis.

The compounds of interest (which can be from any source, including but not limited to combinatorial libraries, natural products, known therapeutic agents, small inorganic molecules, and so forth) can be tested for instance by exposing the novel Lamin A variant described herein, or another variant Lamin A protein, to the compounds, and if a compound inhibits one of the Lamin A variants, the compound is then further evaluated for its anti-disease properties, such as its ability to increase the number of divisions a cell can undergo in culture. In specific examples, the testing method is a high throughput method, for instance an array-based and/or computer enabled method.

One aspect involves a screening method to identify a compound effective for treating, preventing, or ameliorating HGPS or an age-related condition such as arteriosclerosis or athrosclerosis, which method includes ascertaining the compound's inhibition of a provided Lamin A variant or another dominant negative Lamin A variant. In some embodiments, the screening method further includes determining whether the compound increases the growth or life of cells such as fibroblasts in a cell culture. In particular examples of such methods, the culture fibroblasts originated from a subject with HGPS; in others, they are fibroblasts obtained from a subject who is above a median or defined age, or from a subject in a family known to live to above a median or defined age.

In other examples, the screening method includes examining the morphology of the nuclear membrane in cells (such as cells from or derived from a subject known to have progeria or a progeroid condition) treated with a compound of interest, to determine whether the compound alters the morphology. Methods of observing nuclear membrane morphology are well known to those of ordinary skill, and include but are not limited to staining for lamins (e.g., using antibodies or other specific binding agents) or for DNA (e.g., using DAPI). Compounds that make the morphology more like normal (e.g., more like that seen in a cell from a subject (or derived from a subject) known not to have progeria or a progeroid condition) are then selected for further testing and evaluation.

By screening compounds in any of these fashions, potentially beneficial and improved compounds for treating age-related diseases and conditions, including HGPS and other progeroid diseases as well as arteriosclerosis and athrosclerosis, can be identified more rapidly and with greater precision than possible in the past.

This disclosure provides a link between mutations in the LMNA gene, and particularly in Exon 11 of this gene, and the genetic disease HGPS. Other LMNA mutations are also identified that are linked to other progeroid conditions. The disclosure further provides methods of detecting, diagnosing, treating, and otherwise influencing progeria and other aging-related conditions, such as arteriosclerosis or athrosclerosis, based on the identification of alleles of the LMNA gene, or abnormalities in the expression of Lamin A. It will be apparent that the precise details of the methods described may be varied or modified without departing from the spirit of the described invention. We claim all such modifications and variations that fall within the scope and spirit of the claims below.

The invention claimed is:

1. A method of detecting arteriosclerosis, atherosclerosis, predisposition to arteriosclerosis, or predisposition to atherosclerosis in a subject, the method comprising:
   detecting in a sample from the subject, expression of a truncated Lamin A protein or mutant LMNA nucleic acid encoding the truncated Lamin A protein by reacting at least one mutant LMNA nucleic acid molecule in the sample from the subject with a reagent comprising a LMNA nucleic acid-specific binding agent to form a mutant LMNA nucleic acid:agent complex, wherein the truncated Lamin A protein comprises:
   (a) the amino acid sequence set forth as SEQ ID NO: 7;
   (b) an amino acid sequence having at least 95% sequence identity to SEQ ID NO: 7 and containing Mutation 1 (G608G(GGC>GGT)) or Mutation 2 (G608S (GGC>AGC)); or
   (c) a conservative variant of (a) containing Mutation 1 (G608G(GGC>GGT)) or Mutation 2 (G608S (GGC>AGC));
   whereby the expression of the truncated Lamin A protein or mutant LMNA nucleic acid indicates that the subject has or is predisposed to arteriosclerosis or atherosclerosis.

2. The method of claim 1, wherein the truncated Lamin A protein comprises an amino acid sequence comprising G608G(GGC>GGT) or G608S(GGC>AGC).

3. The method of claim 1, wherein the mutant LMNA nucleic acid is RNA.

4. The method of claim 1, wherein the LMNA nucleic acid-specific binding agent is a LMNA-specific oligonucleotide.

* * * * *

SEQUENCE LISTING

```
<160> NUMBER OF SEQ ID NOS: 66

<210> SEQ ID NO 1
<211> LENGTH: 3976
<212> TYPE: DNA
<213> ORGANISM: Homo sapiens
<220> FEATURE:
<221> NAME/KEY: 5'UTR
<222> LOCATION: (1)..(1007)
<220> FEATURE:
<221> NAME/KEY: CDS
<222> LOCATION: (1008)..(3002)
<220> FEATURE:
<221> NAME/KEY: misc_feature
<222> LOCATION: (2670)..(2670)
<223> OTHER INFORMATION: sequence of AH001498 corrected to reflect
      Fisher et al., PNAS USA, 83: 6450-6454, 1986
<220> FEATURE:
<221> NAME/KEY: misc_feature
<222> LOCATION: (2673)..(2673)
<223> OTHER INFORMATION: sequence of AH001498 corrected to reflect
      Fisher et al., PNAS USA, 83: 6450-6454, 1986
<220> FEATURE:
<221> NAME/KEY: misc_feature
<222> LOCATION: (2706)..(2708)
<223> OTHER INFORMATION: First codon of exon 11
<220> FEATURE:
<221> NAME/KEY: misc_feature
<222> LOCATION: (2826)..(2975)
<223> OTHER INFORMATION: region spliced out in mutant form
<220> FEATURE:
<221> NAME/KEY: misc_feature
<222> LOCATION: (2829)..(2931)
<223> OTHER INFORMATION: Codon for amino acid 608

<400> SEQUENCE: 1
gaaggggaca ggagatggaa ggggcagtgc ctggctccta ttcttggctt tctttagggg    60
```

-continued

```
acttctttag gggactgtgg cttgttgctt gggtctaaaa acgaatgctt ggctttgaag      120
agagatagat tggggcaaaa gaaagaaaaa aagggacccc ccaaactcct tgatccctgg      180
ccccaaactg ggggcataaa ggaactcagg ttccaaaact ttgctccccc cagggaaccc      240
aggcattcct tctccacccc actcctggca cactgagatg caggtctgaa tgcgctgccc      300
acgtgtggag gggggttggg gtgactcact attactactg ggaggacagg gggagccagt      360
ggtggaagaa gggtgagtca cactgatggg caccagcctc agccctcccc ccactttcct      420
ggctcccagc cctgcctacc tgaccctctc ccttgctttg cgcccacttc cctctctttc      480
tccccgaccc ttttgcccac ccactctccc tccttggctc tgccctctag cccagaaggt      540
ctgaggcaat gggggcaagc ttggagccga cagtgctgag caggcaggag ccaagagagg      600
ggaagcttga gcctcacgca gttaggggtg cgctggagag ggtggggccc gactccgcca      660
caccccaacg gtccttcccc ctcctcacca ctcccgcccc cacccccaat ggatctggga      720
ctgccccttt aagagtagtg gccccctcctc ccttcagagg aggacctatt agagcctttg      780
ccccggcgtc ggtgactcag tgttcgcggg agcgccgcac ctacaccagc caacccagat      840
cccgaggtcc gacagcgccc ggcccagatc cccacgcctg ccaggagcaa gccgaagagc      900
cagccggccg gcgcactccg actccgagca gtctctgtcc ttcgacccga gccccgcgcc      960
ctttccggga cccctgcccc gcgggcagcg ctgccaacct gccggcc atg gag acc     1016
                                                  Met Glu Thr
                                                    1 ccg tcc cag cgg cgc gcc acc cgc agc ggg gcg cag gcc agc tcc act      1064
Pro Ser Gln Arg Arg Ala Thr Arg Ser Gly Ala Gln Ala Ser Ser Thr
  5                  10                  15 ccg ctg tcg ccc acc cgc atc acc cgg ctg cag gag aag gag gac ctg      1112
Pro Leu Ser Pro Thr Arg Ile Thr Arg Leu Gln Glu Lys Glu Asp Leu
 20                  25                  30                  35 cag gag ctc aat gat cgc ttg gcg gtc tac atc gac cgt gtg cgc tcg      1160
Gln Glu Leu Asn Asp Arg Leu Ala Val Tyr Ile Asp Arg Val Arg Ser
                 40                  45                  50 ctg gaa acg gag aac gca ggg ctg cgc ctt cgc atc acc gag tct gaa      1208
Leu Glu Thr Glu Asn Ala Gly Leu Arg Leu Arg Ile Thr Glu Ser Glu
 55                  60                  65 gag gtg gtc agc cgc gag gtg tcc ggc atc aag gcc gcc tac gag gcc      1256
Glu Val Val Ser Arg Glu Val Ser Gly Ile Lys Ala Ala Tyr Glu Ala
                 70                  75                  80 gag ctc ggg gat gcc cgc aag acc ctt gac tca gta gcc aag gag cgc      1304
Glu Leu Gly Asp Ala Arg Lys Thr Leu Asp Ser Val Ala Lys Glu Arg
 85                  90                  95 gcc cgc ctg cag ctg gag ctg agc aaa gtg cgt gag gag ttt aag gag      1352
Ala Arg Leu Gln Leu Glu Leu Ser Lys Val Arg Glu Glu Phe Lys Glu
100                 105                 110                 115 ctg aaa gcg cgc aat acc aag aag gag ggt gac ctg ata gct gct cag      1400
Leu Lys Ala Arg Asn Thr Lys Lys Glu Gly Asp Leu Ile Ala Ala Gln
                120                 125                 130 gct cgg ctg aag gac ctg gag gct ctg ctg aac tcc aag gag gcc gca      1448
Ala Arg Leu Lys Asp Leu Glu Ala Leu Leu Asn Ser Lys Glu Ala Ala
135                 140                 145 ctg agc act gct ctc agt gag aag cgc acg ctg gag ggc gag ctg cat      1496
Leu Ser Thr Ala Leu Ser Glu Lys Arg Thr Leu Glu Gly Glu Leu His
                150                 155                 160 gat ctg cgg ggc cag gtg gcc aag ctt gag gca gcc cta ggt gag gcc      1544
Asp Leu Arg Gly Gln Val Ala Lys Leu Glu Ala Ala Leu Gly Glu Ala
165                 170                 175 aag aag caa ctt cag gat gag atg ctg cgg cgg gtg gat gct gag aac      1592
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Lys<br>180 | Lys | Gln | Leu | Gln<br>185 | Asp | Glu | Met | Leu | Arg<br>190 | Arg | Val | Asp | Ala | Glu<br>195 | Asn |      |

```
agg ctg cag acc atg aag gag gaa ctg gac ttc cag aag aac atc tac   1640
Arg Leu Gln Thr Met Lys Glu Glu Leu Asp Phe Gln Lys Asn Ile Tyr
            200                 205                 210 agt gag gag ctg cgt gag acc aag cgc cgt cat gag acc cga ctg gtg   1688
Ser Glu Glu Leu Arg Glu Thr Lys Arg Arg His Glu Thr Arg Leu Val
        215                 220                 225 gag att gac aat ggg aag cag cgt gag ttt gag agc cgg ctg gcg gat   1736
Glu Ile Asp Asn Gly Lys Gln Arg Glu Phe Glu Ser Arg Leu Ala Asp
    230                 235                 240 gcg ctg cag gaa ctg cgg gcc cag cat gag gac cag gtg gag cag tat   1784
Ala Leu Gln Glu Leu Arg Ala Gln His Glu Asp Gln Val Glu Gln Tyr
245                 250                 255 aag aag gag ctg gag aag act tat tct gcc aag ctg gac aat gcc agg   1832
Lys Lys Glu Leu Glu Lys Thr Tyr Ser Ala Lys Leu Asp Asn Ala Arg
260                 265                 270                 275 cag tct gct gag agg aac agc aac ctg gtg ggg gct gcc cac gag gag   1880
Gln Ser Ala Glu Arg Asn Ser Asn Leu Val Gly Ala Ala His Glu Glu
            280                 285                 290 ctg cag cag tcg cgc atc cgc atc gac agc ctc tct gcc cag ctc agc   1928
Leu Gln Gln Ser Arg Ile Arg Ile Asp Ser Leu Ser Ala Gln Leu Ser
        295                 300                 305 cag ctc cag aag cag ctg gca gcc aag gag gcg aag ctt cga gac ctg   1976
Gln Leu Gln Lys Gln Leu Ala Ala Lys Glu Ala Lys Leu Arg Asp Leu
    310                 315                 320 gag gac tca ctg gcc cgt gag cgg gac acc agc cgg cgg ctg ctg gcg   2024
Glu Asp Ser Leu Ala Arg Glu Arg Asp Thr Ser Arg Arg Leu Leu Ala
325                 330                 335 gaa aag gag cgg gag atg gcc gag atg cgg gca agg atg cag cag cag   2072
Glu Lys Glu Arg Glu Met Ala Glu Met Arg Ala Arg Met Gln Gln Gln
340                 345                 350                 355 ctg gac gag tac cag gag ctt ctg gac atc aag ctg gcc ctg gac atg   2120
Leu Asp Glu Tyr Gln Glu Leu Leu Asp Ile Lys Leu Ala Leu Asp Met
            360                 365                 370 gag atc cac gcc tac cgc aag ctc ttg gag ggc gag gag gag agg cta   2168
Glu Ile His Ala Tyr Arg Lys Leu Leu Glu Gly Glu Glu Glu Arg Leu
        375                 380                 385 cgc ctg tcc ccc agc cct acc tcg cag cgc agc cgt ggc cgt gct tcc   2216
Arg Leu Ser Pro Ser Pro Thr Ser Gln Arg Ser Arg Gly Arg Ala Ser
    390                 395                 400 tct cac tca tcc cag aca cag ggt ggg ggc agc gtc acc aaa aag cgc   2264
Ser His Ser Ser Gln Thr Gln Gly Gly Gly Ser Val Thr Lys Lys Arg
405                 410                 415 aaa ctg gag tcc act gag agc cgc agc agc ttc tca cag cac gca cgc   2312
Lys Leu Glu Ser Thr Glu Ser Arg Ser Ser Phe Ser Gln His Ala Arg
420                 425                 430                 435 act agc ggg cgc gtg gcc gtg gag gag gtg gat gag gag ggc aag ttt   2360
Thr Ser Gly Arg Val Ala Val Glu Glu Val Asp Glu Glu Gly Lys Phe
            440                 445                 450 gtc cgg ctg cgc aac aag tcc aat gag gac cag tcc atg ggc aat tgg   2408
Val Arg Leu Arg Asn Lys Ser Asn Glu Asp Gln Ser Met Gly Asn Trp
        455                 460                 465 cag atc aag cgc cag aat gga gat gat ccc ttg ctg act tac cgg ttc   2456
Gln Ile Lys Arg Gln Asn Gly Asp Asp Pro Leu Leu Thr Tyr Arg Phe
    470                 475                 480 cca cca aag ttc acc ctg aag gct ggg cag gtg gtg acg atc tgg gct   2504
Pro Pro Lys Phe Thr Leu Lys Ala Gly Gln Val Val Thr Ile Trp Ala
485                 490                 495 gca gga gct ggg gcc acc cac agc ccc cct acc gac ctg gtg tgg aag   2552
```

```
                Ala Gly Ala Gly Ala Thr His Ser Pro Pro Thr Asp Leu Val Trp Lys
                500                 505                 510                 515 gca cag aac acc tgg ggc tgc ggg aac agc ctg cgt acg gct ctc atc            2600
Ala Gln Asn Thr Trp Gly Cys Gly Asn Ser Leu Arg Thr Ala Leu Ile
                520                 525                 530 aac tcc act ggg gaa gaa gtg gcc atg cgc aag ctg gtg cgc tca gtg            2648
Asn Ser Thr Gly Glu Glu Val Ala Met Arg Lys Leu Val Arg Ser Val
                535                 540                 545 act gtg gtt gag gac gac gag gat gag gat gga gat gac ctc ctc cat            2696
Thr Val Val Glu Asp Asp Glu Asp Glu Asp Gly Asp Asp Leu Leu His
                550                 555                 560 cac cac cac ggc tcc cac tgc agc agc tcg ggg gac ccc gct gag tac            2744
His His His Gly Ser His Cys Ser Ser Ser Gly Asp Pro Ala Glu Tyr
                565                 570                 575 aac ctg cgc tcg cgc acc gtg ctg tgc ggg acc tgc ggg cag cct gcc            2792
Asn Leu Arg Ser Arg Thr Val Leu Cys Gly Thr Cys Gly Gln Pro Ala
580                 585                 590                 595 gac aag gca tct gcc agc ggc tca gga gcc cag gtg ggc gga ccc atc            2840
Asp Lys Ala Ser Ala Ser Gly Ser Gly Ala Gln Val Gly Gly Pro Ile
                600                 605                 610 tcc tct ggc tct tct gcc tcc agt gtc acg gtc act cgc agc tac cgc            2888
Ser Ser Gly Ser Ser Ala Ser Ser Val Thr Val Thr Arg Ser Tyr Arg
                615                 620                 625 agt gtg ggg ggc agt ggg ggt ggc agc ttc ggg gac aat ctg gtc acc            2936
Ser Val Gly Gly Ser Gly Gly Gly Ser Phe Gly Asp Asn Leu Val Thr
                630                 635                 640 cgc tcc tac ctc ctg ggc aac tcc agc ccc cga acc cag agc ccc cag            2984
Arg Ser Tyr Leu Leu Gly Asn Ser Ser Pro Arg Thr Gln Ser Pro Gln
                645                 650                 655 aac tgc agc atc atg taa tctgggacct gccaggcagg ggtgggggtg                   3032
Asn Cys Ser Ile Met
660 gaggcttcct gcgtcctcct cacctcatgc ccaccccctg ccctgcacgt catgggaggg          3092 ggcttgaagc caaagaaaaa taacccttg gttttttct tctgtatttg tttttctaag            3152 agaagttatt ttctacagtg gtttatact gaaggaaaaa cacaagcaaa aaaaaaaaa            3212 aagcatctat ctcatctatc tcaatcctaa tttctcctcc cttcctttc cctgcttcca           3272 ggaaactcca catctgcctt aaaaccaaag agggcttcct ctagaagcca agggaaaggg          3332 gtgctttat agaggctagc ttctgctttt ctgccctggc tgctgcccca ccccggggac           3392 cctgtgacat ggtgcctgag aggcaggcat agaggcttct ccgccagcct cctctggacg         3452 gcaggctcac tgccaggcca gcctccgaga gggagagaga gagagagagg acagcttgag         3512 ccgggcccct ggcttggcct gctgtgattc cactacacct ggctgaggtt cctctgcctg         3572 ccccgccccc agtccccacc cctgccccca gccccggggt gagtccattc tcccaggtac         3632 cagctgcgct tgcttttctg tatttattt agacaagaga tgggaatgag gtgggaggtg          3692 gaagaaggga gaagaaaggt gagtttgagc tgccttccct agctttagac cctgggtggg         3752 ctctgtgcag tcactggagg ttgaagccaa gtgggtgct gggaggaggg agagggaggt          3812 cactggaaag gggagagcct gctgcaccca ccgtggagga ggaaggcaag aggggtggga         3872 ggggtgtggc agttggtttt ggcaaacgct taaagagccc ttgcctcccc atttcccatc         3932 tgcacccctt ctctcctccc caaatcaata cactagttgt ttct                          3976

<210> SEQ ID NO 2
<211> LENGTH: 664
<212> TYPE: PRT
<213> ORGANISM: Homo sapiens
```

<400> SEQUENCE: 2

```
Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
            20                  25                  30

Glu Asp Leu Gln Glu Leu Asn Asp Arg Leu Ala Val Tyr Ile Asp Arg
        35                  40                  45

Val Arg Ser Leu Glu Thr Glu Asn Ala Gly Leu Arg Leu Arg Ile Thr
    50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
    210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
    290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
    370                 375                 380

Glu Arg Leu Arg Leu Ser Pro Ser Pro Thr Ser Gln Arg Ser Arg Gly
385                 390                 395                 400

Arg Ala Ser Ser His Ser Ser Gln Thr Gln Gly Gly Gly Ser Val Thr
                405                 410                 415
```

```
Lys Lys Arg Lys Leu Glu Ser Thr Glu Ser Arg Ser Ser Phe Ser Gln
        420                 425                 430

His Ala Arg Thr Ser Gly Arg Val Ala Val Glu Glu Val Asp Glu Glu
            435                 440                 445

Gly Lys Phe Val Arg Leu Arg Asn Lys Ser Asn Glu Asp Gln Ser Met
    450                 455                 460

Gly Asn Trp Gln Ile Lys Arg Gln Asn Gly Asp Asp Pro Leu Leu Thr
465                 470                 475                 480

Tyr Arg Phe Pro Pro Lys Phe Thr Leu Lys Ala Gly Gln Val Val Thr
                485                 490                 495

Ile Trp Ala Ala Gly Ala Gly Ala Thr His Ser Pro Pro Thr Asp Leu
                500                 505                 510

Val Trp Lys Ala Gln Asn Thr Trp Gly Cys Gly Asn Ser Leu Arg Thr
            515                 520                 525

Ala Leu Ile Asn Ser Thr Gly Glu Glu Val Ala Met Arg Lys Leu Val
        530                 535                 540

Arg Ser Val Thr Val Val Glu Asp Asp Glu Asp Glu Asp Gly Asp Asp
545                 550                 555                 560

Leu Leu His His His Gly Ser His Cys Ser Ser Ser Gly Asp Pro
                565                 570                 575

Ala Glu Tyr Asn Leu Arg Ser Arg Thr Val Leu Cys Gly Thr Cys Gly
            580                 585                 590

Gln Pro Ala Asp Lys Ala Ser Ala Ser Gly Ser Gly Ala Gln Val Gly
                595                 600                 605

Gly Pro Ile Ser Ser Gly Ser Ser Ala Ser Ser Val Thr Val Thr Arg
    610                 615                 620

Ser Tyr Arg Ser Val Gly Gly Ser Gly Gly Gly Ser Phe Gly Asp Asn
625                 630                 635                 640

Leu Val Thr Arg Ser Tyr Leu Leu Gly Asn Ser Ser Pro Arg Thr Gln
                645                 650                 655

Ser Pro Gln Asn Cys Ser Ile Met
            660

<210> SEQ ID NO 3
<211> LENGTH: 270
<212> TYPE: DNA
<213> ORGANISM: Homo sapiens
<220> FEATURE:
<221> NAME/KEY: misc_feature
<222> LOCATION: (124)..(126)
<223> OTHER INFORMATION: codon for amino acid 608

<400> SEQUENCE: 3
ggctcccact gcagcagctc gggggacccc gctgagtaca acctgcgctc gcgcaccgtg      60
ctgtgcggga cctgcgggca gcctgccgac aaggcatctg ccagcggctc aggagcccag     120
gtgggcggac ccatctcctc tggctcttct gcctccagtg tcacggtcac tcgcagctac     180
cgcagtgtgg ggggcagtgg gggtggcagc ttcggggaca atctggtcac ccgctcctac     240
ctcctgggca actccagccc ccgaacccag                                      270

<210> SEQ ID NO 4
<211> LENGTH: 270
<212> TYPE: DNA
<213> ORGANISM: Homo sapiens
<220> FEATURE:
<221> NAME/KEY: mutation
<222> LOCATION: (126)..(126)
<223> OTHER INFORMATION: mutation leading to classical HGPS; C in
``` wildtype, T in mutant

<400> SEQUENCE: 4

```
ggctcccact gcagcagctc gggggacccc gctgagtaca acctgcgctc gcgcaccgtg    60
ctgtgcggga cctgcgggca gcctgccgac aaggcatctg ccagcggctc aggagcccag   120
gtgggyggac ccatctcctc tggctcttct gcctccagtg tcacggtcac tcgcagctac   180
cgcagtgtgg ggggcagtgg gggtggcagc ttcggggaca atctggtcac ccgctcctac   240
ctcctgggca actccagccc ccgaacccag                                    270
```

<210> SEQ ID NO 5
<211> LENGTH: 270
<212> TYPE: DNA
<213> ORGANISM: Homo sapiens
<220> FEATURE:
<221> NAME/KEY: mutation
<222> LOCATION: (124)..(124)
<223> OTHER INFORMATION: mutation leading to classical HGPS; A in
      wildtype, G in mutant

<400> SEQUENCE: 5

```
ggctcccact gcagcagctc gggggacccc gctgagtaca acctgcgctc gcgcaccgtg    60
ctgtgcggga cctgcgggca gcctgccgac aaggcatctg ccagcggctc aggagcccag   120
gtgrgcggac ccatctcctc tggctcttct gcctccagtg tcacggtcac tcgcagctac   180
cgcagtgtgg ggggcagtgg gggtggcagc ttcggggaca atctggtcac ccgctcctac   240
ctcctgggca actccagccc ccgaacccag                                    270
```

<210> SEQ ID NO 6
<211> LENGTH: 2819
<212> TYPE: DNA
<213> ORGANISM: Homo sapiens
<220> FEATURE:
<221> NAME/KEY: CDS
<222> LOCATION: (1)..(1845)
<223> OTHER INFORMATION: mutant Lamin A encoding sequence

<400> SEQUENCE: 6

```
atg gag acc ccg tcc cag cgg cgc gcc acc cgc agc ggg gcg cag gcc     48
Met Glu Thr Pro Ser Gln Arg Arg Ala Thr Arg Ser Gly Ala Gln Ala
1               5                   10                  15 agc tcc act ccg ctg tcg ccc acc cgc atc acc cgg ctg cag gag aag     96
Ser Ser Thr Pro Leu Ser Pro Thr Arg Ile Thr Arg Leu Gln Glu Lys
                20                  25                  30 gag gac ctg cag gag ctc aat gat cgc ttg gcg gtc tac atc gac cgt    144
Glu Asp Leu Gln Glu Leu Asn Asp Arg Leu Ala Val Tyr Ile Asp Arg
            35                  40                  45 gtg cgc tcg ctg gaa acg gag aac gca ggg ctg cgc ctt cgc atc acc    192
Val Arg Ser Leu Glu Thr Glu Asn Ala Gly Leu Arg Leu Arg Ile Thr
        50                  55                  60 gag tct gaa gag gtg gtc agc cgc gag gtg tcc ggc atc aag gcc gcc    240
Glu Ser Glu Glu Val Val Ser Arg Glu Val Ser Gly Ile Lys Ala Ala
65                  70                  75                  80 tac gag gcc gag ctc ggg gat gcc cgc aag acc ctt gac tca gta gcc    288
Tyr Glu Ala Glu Leu Gly Asp Ala Arg Lys Thr Leu Asp Ser Val Ala
                85                  90                  95 aag gag cgc gcc cgc ctg cag ctg gag ctg agc aaa gtg cgt gag gag    336
Lys Glu Arg Ala Arg Leu Gln Leu Glu Leu Ser Lys Val Arg Glu Glu
                100                 105                 110 ttt aag gag ctg aaa gcg cgc aat acc aag aag gag ggt gac ctg ata    384
Phe Lys Glu Leu Lys Ala Arg Asn Thr Lys Lys Glu Gly Asp Leu Ile
            115                 120                 125
```

| | | |
|---|---|---|
| gct gct cag gct cgg ctg aag gac ctg gag gct ctg ctg aac tcc aag<br>Ala Ala Gln Ala Arg Leu Lys Asp Leu Glu Ala Leu Leu Asn Ser Lys<br>130                         135                     140 | 432 |
| gag gcc gca ctg agc act gct ctc agt gag aag cgc acg ctg gag ggc<br>Glu Ala Ala Leu Ser Thr Ala Leu Ser Glu Lys Arg Thr Leu Glu Gly<br>145                    150                     155                 160 | 480 |
| gag ctg cat gat ctg cgg ggc cag gtg gcc aag ctt gag gca gcc cta<br>Glu Leu His Asp Leu Arg Gly Gln Val Ala Lys Leu Glu Ala Ala Leu<br>                     165                     170                     175 | 528 |
| ggt gag gcc aag aag caa ctt cag gat gag atg ctg cgg cgg gtg gat<br>Gly Glu Ala Lys Lys Gln Leu Gln Asp Glu Met Leu Arg Arg Val Asp<br>             180                     185                     190 | 576 |
| gct gag aac agg ctg cag acc atg aag gag gaa ctg gac ttc cag aag<br>Ala Glu Asn Arg Leu Gln Thr Met Lys Glu Glu Leu Asp Phe Gln Lys<br>                     195                     200                     205 | 624 |
| aac atc tac agt gag gag ctg cgt gag acc aag cgc cgt cat gag acc<br>Asn Ile Tyr Ser Glu Glu Leu Arg Glu Thr Lys Arg Arg His Glu Thr<br>210                         215                     220 | 672 |
| cga ctg gtg gag att gac aat ggg aag cag cgt gag ttt gag agc cgg<br>Arg Leu Val Glu Ile Asp Asn Gly Lys Gln Arg Glu Phe Glu Ser Arg<br>225                         230                     235                 240 | 720 |
| ctg gcg gat gcg ctg cag gaa ctg cgg gcc cag cat gag gac cag gtg<br>Leu Ala Asp Ala Leu Gln Glu Leu Arg Ala Gln His Glu Asp Gln Val<br>                     245                     250                     255 | 768 |
| gag cag tat aag aag gag ctg gag aag act tat tct gcc aag ctg gac<br>Glu Gln Tyr Lys Lys Glu Leu Glu Lys Thr Tyr Ser Ala Lys Leu Asp<br>             260                     265                     270 | 816 |
| aat gcc agg cag tct gct gag agg aac agc aac ctg gtg ggg gct gcc<br>Asn Ala Arg Gln Ser Ala Glu Arg Asn Ser Asn Leu Val Gly Ala Ala<br>                 275                     280                     285 | 864 |
| cac gag gag ctg cag cag tcg cgc atc cgc atc gac agc ctc tct gcc<br>His Glu Glu Leu Gln Gln Ser Arg Ile Arg Ile Asp Ser Leu Ser Ala<br>             290                     295                     300 | 912 |
| cag ctc agc cag ctc cag aag cag ctg gca gcc aag gag gcg aag ctt<br>Gln Leu Ser Gln Leu Gln Lys Gln Leu Ala Ala Lys Glu Ala Lys Leu<br>305                         310                     315                 320 | 960 |
| cga gac ctg gag gac tca ctg gcc cgt gag cgg gac acc agc cgg cgg<br>Arg Asp Leu Glu Asp Ser Leu Ala Arg Glu Arg Asp Thr Ser Arg Arg<br>                     325                     330                     335 | 1008 |
| ctg ctg gcg gaa aag gag cgg gag atg gcc gag atg cgg gca agg atg<br>Leu Leu Ala Glu Lys Glu Arg Glu Met Ala Glu Met Arg Ala Arg Met<br>             340                     345                     350 | 1056 |
| cag cag cag ctg gac gag tac cag gag ctt ctg gac atc aag ctg gcc<br>Gln Gln Gln Leu Asp Glu Tyr Gln Glu Leu Leu Asp Ile Lys Leu Ala<br>                 355                     360                     365 | 1104 |
| ctg gac atg gag atc cac gcc tac cgc aag ctc ttg gag ggc gag gag<br>Leu Asp Met Glu Ile His Ala Tyr Arg Lys Leu Leu Glu Gly Glu Glu<br>370                         375                     380 | 1152 |
| gag agg cta cgc ctg tcc ccc agc cct acc tcg cag cgc agc cgt ggc<br>Glu Arg Leu Arg Leu Ser Pro Ser Pro Thr Ser Gln Arg Ser Arg Gly<br>385                         390                     395                 400 | 1200 |
| cgt gct tcc tct cac tca tcc cag aca cag ggt ggg ggc agc gtc acc<br>Arg Ala Ser Ser His Ser Ser Gln Thr Gln Gly Gly Gly Ser Val Thr<br>                     405                     410                     415 | 1248 |
| aaa aag cgc aaa ctg gag tcc act gag agc cgc agc agc ttc tca cag<br>Lys Lys Arg Lys Leu Glu Ser Thr Glu Ser Arg Ser Ser Phe Ser Gln<br>             420                     425                     430 | 1296 |
| cac gca cgc act agc ggg cgc gtg gcc gtg gag gag gtg gat gag gag<br>His Ala Arg Thr Ser Gly Arg Val Ala Val Glu Glu Val Asp Glu Glu<br>                 435                     440                     445 | 1344 |

```
ggc aag ttt gtc cgg ctg cgc aac aag tcc aat gag gac cag tcc atg    1392
Gly Lys Phe Val Arg Leu Arg Asn Lys Ser Asn Glu Asp Gln Ser Met
    450                 455                 460 ggc aat tgg cag atc aag cgc cag aat gga gat gat ccc ttg ctg act    1440
Gly Asn Trp Gln Ile Lys Arg Gln Asn Gly Asp Asp Pro Leu Leu Thr
465                 470                 475                 480 tac cgg ttc cca cca aag ttc acc ctg aag gct ggg cag gtg gtg acg    1488
Tyr Arg Phe Pro Pro Lys Phe Thr Leu Lys Ala Gly Gln Val Val Thr
                485                 490                 495 atc tgg gct gca gga gct ggg gcc acc cac agc ccc cct acc gac ctg    1536
Ile Trp Ala Ala Gly Ala Gly Ala Thr His Ser Pro Pro Thr Asp Leu
            500                 505                 510 gtg tgg aag gca cag aac acc tgg ggc tgc ggg aac agc ctg cgt acg    1584
Val Trp Lys Ala Gln Asn Thr Trp Gly Cys Gly Asn Ser Leu Arg Thr
        515                 520                 525 gct ctc atc aac tcc act ggg gaa gaa gtg gcc atg cgc aag ctg gtg    1632
Ala Leu Ile Asn Ser Thr Gly Glu Glu Val Ala Met Arg Lys Leu Val
    530                 535                 540 cgc tca gtg act gtg gtt gag gac gac gag gat gag gat gga gat gac    1680
Arg Ser Val Thr Val Val Glu Asp Asp Glu Asp Glu Asp Gly Asp Asp
545                 550                 555                 560 ctg ctc cat cac cac cac ggc tcc cac tgc agc agc tcg ggg gac ccc    1728
Leu Leu His His His His Gly Ser His Cys Ser Ser Ser Gly Asp Pro
                565                 570                 575 gct gag tac aac ctg cgc tcg cgc acc gtg ctg tgc ggg acc tgc ggg    1776
Ala Glu Tyr Asn Leu Arg Ser Arg Thr Val Leu Cys Gly Thr Cys Gly
            580                 585                 590 cag cct gcc gac aag gca tct gcc agc ggc tca gga gcc cag agc ccc    1824
Gln Pro Ala Asp Lys Ala Ser Ala Ser Gly Ser Gly Ala Gln Ser Pro
        595                 600                 605 cag aac tgc agc atc atg taa tctgggacct gccaggcagg ggtgggggtg       1875
Gln Asn Cys Ser Ile Met
    610 gaggcttcct gcgtcctcct cacctcatgc ccaccccctg ccctgcacgt catgggaggg    1935 ggcttgaagc caaagaaaaa taacccttg gttttttttct tctgtatttg tttttctaag   1995 agaagttatt ttctacagtg gttttatact gaaggaaaaa cacaagcaaa aaaaaaaaa    2055 aagcatctat ctcatctatc tcaatcctaa tttctcctcc cttcctttc cctgcttcca    2115 ggaaactcca catctgcctt aaaaccaaag agggcttcct ctagaagcca agggaaaggg   2175 gtgcttttat agaggctagc ttctgctttt ctgccctggc tgctgcccca ccccggggac   2235 cctgtgacat ggtgcctgag aggcaggcat agaggcttct ccgccagcct cctctggacg   2295 gcaggctcac tgccaggcca gcctccgaga gggagagaga gagagagagg acagcttgag   2355 ccgggcccct ggcttggcct gctgtgattc cactacacct ggctgaggtt cctctgcctg   2415 ccccgccccc agtccccacc cctgccccca gccccggggt gagtccattc tcccaggtac   2475 cagctgcgct tgcttttctg tattttattt agacaagaga tgggaatgag gtgggaggtg   2535 gaagaaggga gaagaaaggt gagtttgagc tgccttccct agctttagac cctgggtggg   2595 ctctgtgcag tcactggagg ttgaagccaa gtggggtgct gggaggaggg agaggaggt   2655 cactggaaag gggagagcct gctgcaccca ccgtggagga ggaaggcaag aggggtgga   2715 ggggtgtggc agttggtttt ggcaaacgct taaagagccc ttgcctcccc atttcccatc   2775 tgcaccccctt ctctcctccc caaatcaata cactagttgt ttct                 2819

<210> SEQ ID NO 7
<211> LENGTH: 614
```

```
<212> TYPE: PRT
<213> ORGANISM: Homo sapiens

<400> SEQUENCE: 7

Met Glu Thr Pro Ser Gln Arg Arg Ala Thr Arg Ser Gly Ala Gln Ala
1               5                   10                  15

Ser Ser Thr Pro Leu Ser Pro Thr Arg Ile Thr Arg Leu Gln Glu Lys
                20                  25                  30

Glu Asp Leu Gln Glu Leu Asn Asp Arg Leu Ala Val Tyr Ile Asp Arg
            35                  40                  45

Val Arg Ser Leu Glu Thr Glu Asn Ala Gly Leu Arg Leu Arg Ile Thr
50                  55                  60

Glu Ser Glu Glu Val Val Ser Arg Glu Val Ser Gly Ile Lys Ala Ala
65                  70                  75                  80

Tyr Glu Ala Glu Leu Gly Asp Ala Arg Lys Thr Leu Asp Ser Val Ala
                85                  90                  95

Lys Glu Arg Ala Arg Leu Gln Leu Glu Leu Ser Lys Val Arg Glu Glu
            100                 105                 110

Phe Lys Glu Leu Lys Ala Arg Asn Thr Lys Lys Glu Gly Asp Leu Ile
        115                 120                 125

Ala Ala Gln Ala Arg Leu Lys Asp Leu Glu Ala Leu Leu Asn Ser Lys
130                 135                 140

Glu Ala Ala Leu Ser Thr Ala Leu Ser Glu Lys Arg Thr Leu Glu Gly
145                 150                 155                 160

Glu Leu His Asp Leu Arg Gly Gln Val Ala Lys Leu Glu Ala Ala Leu
                165                 170                 175

Gly Glu Ala Lys Lys Gln Leu Gln Asp Glu Met Leu Arg Arg Val Asp
            180                 185                 190

Ala Glu Asn Arg Leu Gln Thr Met Lys Glu Glu Leu Asp Phe Gln Lys
        195                 200                 205

Asn Ile Tyr Ser Glu Glu Leu Arg Glu Thr Lys Arg Arg His Glu Thr
210                 215                 220

Arg Leu Val Glu Ile Asp Asn Gly Lys Gln Arg Glu Phe Glu Ser Arg
225                 230                 235                 240

Leu Ala Asp Ala Leu Gln Glu Leu Arg Ala Gln His Glu Asp Gln Val
                245                 250                 255

Glu Gln Tyr Lys Lys Glu Leu Glu Lys Thr Tyr Ser Ala Lys Leu Asp
            260                 265                 270

Asn Ala Arg Gln Ser Ala Glu Arg Asn Ser Asn Leu Val Gly Ala Ala
        275                 280                 285

His Glu Glu Leu Gln Gln Ser Arg Ile Arg Ile Asp Ser Leu Ser Ala
290                 295                 300

Gln Leu Ser Gln Leu Gln Lys Gln Leu Ala Ala Lys Glu Ala Lys Leu
305                 310                 315                 320

Arg Asp Leu Glu Asp Ser Leu Ala Arg Glu Arg Asp Thr Ser Arg Arg
                325                 330                 335

Leu Leu Ala Glu Lys Glu Arg Glu Met Ala Glu Met Arg Ala Arg Met
            340                 345                 350

Gln Gln Gln Leu Asp Glu Tyr Gln Glu Leu Leu Asp Ile Lys Leu Ala
        355                 360                 365

Leu Asp Met Glu Ile His Ala Tyr Arg Lys Leu Leu Glu Gly Glu Glu
370                 375                 380

Glu Arg Leu Arg Leu Ser Pro Ser Pro Thr Ser Gln Arg Ser Arg Gly
385                 390                 395                 400
```

```
Arg Ala Ser Ser His Ser Ser Gln Thr Gln Gly Gly Ser Val Thr
                405                 410                 415
Lys Lys Arg Lys Leu Glu Ser Thr Glu Ser Arg Ser Ser Phe Ser Gln
        420                 425                 430
His Ala Arg Thr Ser Gly Arg Val Ala Val Glu Glu Val Asp Glu Glu
        435                 440                 445
Gly Lys Phe Val Arg Leu Arg Asn Lys Ser Asn Glu Asp Gln Ser Met
    450                 455                 460
Gly Asn Trp Gln Ile Lys Arg Gln Asn Gly Asp Asp Pro Leu Leu Thr
465                 470                 475                 480
Tyr Arg Phe Pro Pro Lys Phe Thr Leu Lys Ala Gly Gln Val Val Thr
                485                 490                 495
Ile Trp Ala Ala Gly Ala Gly Ala Thr His Ser Pro Pro Thr Asp Leu
            500                 505                 510
Val Trp Lys Ala Gln Asn Thr Trp Gly Cys Gly Asn Ser Leu Arg Thr
        515                 520                 525
Ala Leu Ile Asn Ser Thr Gly Glu Glu Val Ala Met Arg Lys Leu Val
    530                 535                 540
Arg Ser Val Thr Val Val Glu Asp Asp Glu Asp Glu Asp Gly Asp Asp
545                 550                 555                 560
Leu Leu His His His His Gly Ser His Cys Ser Ser Ser Gly Asp Pro
                565                 570                 575
Ala Glu Tyr Asn Leu Arg Ser Arg Thr Val Leu Cys Gly Thr Cys Gly
            580                 585                 590
Gln Pro Ala Asp Lys Ala Ser Ala Ser Gly Ser Gly Ala Gln Ser Pro
        595                 600                 605
Gln Asn Cys Ser Ile Met
    610

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ggatgcatct gtgattgtgg                                             20

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
cccaacaatg aaatgacaca g                                           21

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
agatgaaggc tttgggaggt                                             20

<210> SEQ ID NO 11
```

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ccttgccaag aaagatccag                                                   20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
tgctacactg gggaaccaat                                                   20

<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
gtgagccgag gtcacacc                                                     18

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
agcaaaggcg ttgaatcact                                                   20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
ctgtcttaag cctccctcca                                                   20

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
gaaagaatga caacctgtct caa                                               23

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
```
ccaaatttca gactctggtg a                                         21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
tagatgccat ccagtcacca                                           20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gagctaagat caggccgttg                                           20

<210> SEQ ID NO 20
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 20
agtgctggga ggcatgag                                             18

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gtctcatggg aggtgcattt                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
aaactttgac acccctcagc                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
tgtccaaagg tgcatcatgt                                           20

<210> SEQ ID NO 24
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 24
ggcagcaaaa gtgaaaacaa                                                    20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
cagctcatgt gcctttcctt                                                    20

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26
cctgggcaac aagagtgaa                                                     19

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tctgcatctg gaattgtgga                                                    20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
atgccagcat ccagagagat                                                    20

<210> SEQ ID NO 29
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 29
aagtgattgt agggttggga ttt                                                23

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
ttgtcatctt atgtgccaag g                                                  21

<210> SEQ ID NO 31

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
tccaacctag cttcccttca                                                    20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
ttactgccag gctcagtgtg                                                    20

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
gactgggcta acactgggct a                                                  21

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
gcaagagaag cctggccaat a                                                  21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35
gagcatgatt gggttctggt g                                                  21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
gcagcacaga acccacaggt a                                                  21

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37
```

-continued gtttgatgtt agcagccact ga                                    22

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
gagtgattca acgcctttgc t                                     21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
gcctcatgat cctcccgtct c                                     21

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 40
gtatttgagg caggtcggtg t                                     21

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
ggtcgacaca gcctcactgt                                       20

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
gattcgtttt cctggctttg a                                     21

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
gccagttgtg ttaccgacct                                       20

<210> SEQ ID NO 44
<211> LENGTH: 21
<212> TYPE: DNA
<213> ORGANISM: Artificial Sequence
<220> FEATURE:

-continued

<223> OTHER INFORMATION: Synthetic oligonucleotide

<400> SEQUENCE: 44
gccaggacac ccagctaatt t                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 45
gtcgggagac tgaggtgaga t                                              21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
gaggcagagt gagcagagac c                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 47
gagctcctcg tggatcgtag a                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
ggaaagaagt gaccaatcag g                                              21

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gtctccagca cattccaaag                                                20

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
gttgtagcgg gcgtctgtag t                                              21

<210> SEQ ID NO 51

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51 gtcctttttta tttttgtggt gtcaa                                         25

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
gcatacacag aaaccggaat                                                20

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
gaaagtttgc aggcgatgac t                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 54
gtcaaaatgg caacagcgta a                                              21

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
ggaaagagag gacgggattc                                                20

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 56
gccagccaat gacagatttg a                                              21

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
```
gtattcccag cagcaagtgg                                                  20

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
agcactcagc tcccaggtta                                                  20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 59
ctgatcccca gaaggcatag                                                  20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 60
gtccctcctt ccccatactt                                                  20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 61
ccaagtgggg gtctagtcaa                                                  20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 62
aggtgctggc agtgtcctct                                                  20

<210> SEQ ID NO 63
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 63
ctctgagggc aaggatgttc                                                  20

<210> SEQ ID NO 64
<211> LENGTH: 22
<212> TYPE: DNA
<213> ORGANISM: Artificial Sequence
<220> FEATURE:

```
<223> OTHER INFORMATION: Synthetic oligonucleotide

<400> SEQUENCE: 64
gcaacaagtc caatgaggac ca                                              22

<210> SEQ ID NO 65
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 65
gtcccagatt acatgatgc                                                  19

<210> SEQ ID NO 66
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(4)
<223> OTHER INFORMATION: The X at positions 2 and 3 can be any aliphatic
      amino acid; the X at position 4 can be any amino acid.

<400> SEQUENCE: 66

Cys Xaa Xaa Xaa
1
```